(12) United States Patent
Hoey et al.

(10) Patent No.: US 8,268,569 B2
(45) Date of Patent: Sep. 18, 2012

(54) **RECOMBINANT 15-KDA POLYPEPTIDE AND USE OF SAME IN DETECTING HUMAN INFECTION WITH *BARTONELLA HENSELAE***

(75) Inventors: John G. Hoey, Elmer, NJ (US); Lisa P. Huang, Princeton, NJ (US); Martin E. Adelson, Belle Mead, NJ (US); Eli Mordechai, Robbinsville, NJ (US)

(73) Assignee: Medical Diagnostic Laboratories, L.L.C., Hamilton, NJ (US)

( * ) Notice: Subject to any disclaimer, the term of this patent is extended or adjusted under 35 U.S.C. 154(b) by 0 days.

(21) Appl. No.: 12/462,647

(22) Filed: Aug. 6, 2009

(65) Prior Publication Data
US 2010/0209936 A1    Aug. 19, 2010

Related U.S. Application Data

(60) Provisional application No. 61/189,803, filed on Aug. 22, 2008.

(51) Int. Cl.
*G01N 33/53* (2006.01)
(52) U.S. Cl. ............ 435/7.1; 435/6; 435/7.2; 435/7.32; 435/7.92; 435/69.1; 435/71.1
(58) Field of Classification Search .................. None
See application file for complete search history.

(56) References Cited

FOREIGN PATENT DOCUMENTS
WO    WO01/92535 A1    12/2001

OTHER PUBLICATIONS

Rinas et al (Applied Microbiol. Biotech. 1989. vol. 31, No. 2, 163-167).*
Chou et al (Biotechnol. Prog., 1994, 10 (6), pp. 644-647).*
International Searching Authority, International Search Report, Mar. 15, 2010, pp. 1-5.
International Searching Authority, Written Opinion of the International Searching Authority, Mar. 15, 2010, pp. 1-3.
Haimerl, M. et al. Seroprevalence of *Bartonella henselae* in cats in Germany, J. Med. Microbiol., 1999, pp. 849-856, vol. 48.
Loa, C. C. et al. Diagnostic Microbiology and Infectious Disease, 2006, pp. 1-7, vol. 55.
Kingsman, A. J. et al. Replication in *Saccharomyces cerevisiae* of Plasmid pBR313 Carrying DNA from the Yeast trp1 Region, Gene, 1979, pp. 141-152, vol. 7.
Alsmark, C. M. et al. PNAS, 2004, pp. 9716-9721, vol. 101, No. 26.
Stinchcomb, D. T. et al. Isolation and Characterization of a Yeast Chromosomal Replicator, Nature, 1979, pp. 39-43, vol. 282.
Urlaub, G. et al. Isolation of Chinese Hamster Cell Mutants Deficient in Dihydrofolate Reductase Activity, PNAS, 1980, pp. 4216-4220, vol. 77, No. 7.

* cited by examiner

*Primary Examiner* — Jennifer Graser
(74) *Attorney, Agent, or Firm* — Siu K. Lo, Esq.

(57) ABSTRACT

Disclosed are the cloning and expression of a novel antigen of *Bartonella henselae*. The recombinant polypeptide is found to be highly immunogenic and is useful as a diagnostic test antigen. The polypeptide of the present invention provides the basis of a diagnostic assay that is sensitive, rapid and accurate diagnosis of infection with *Bartonella henselae* using patient's sera. Disclosed also are the ELISA for both IgG and IgM and allows diagnosis of early and late infection.

11 Claims, 19 Drawing Sheets

Figure 2

*Bartonella henselae* str. Houston-1, GeneID: 2865504 (SEQ ID NO: 1)

```
ATGGTGCATT TTGTAAGATG TATTCAGAAC AAGATCCCCC ATGCACTCCC    50
TATGAGTTCA TGCGTTGTAT TTAAAAGTAT CTATGAGTTT AAAAAAATGA   100
AACAAAAAAT AACTTTTGTT ATGATCCTGA TAATTGCCCT TACAGGCTGC   150
GCCTCTCTTA CTGGCCCCAA AAAACCACCA AGATGTAATG GCAAAGTTAC   200
CCGCGCTTTA AATAGAGATA AATGGGATTG GGACAATAAA AACCTCATCC   250
TACAAGAAAA AAATGTAAAG CCTGTCAGGA CTCCTATCAT CCTCAACACG   300
CTGGAAAACG AAAAAGCAAC AGCGACCGTG ACGTTGAAGG AAAATTCATT   350
GAATTCCATA ACTCGTGAAA CACTCCCTGA GAACACTATG GAGATTGCGC   400
GTGAAAATTA A                                             411
```

Figure 3

*Bartonella henselae* str. Houston-1; 15-kDa protein, accession # YP_034056.1 (SEQ ID NO:2)

| | | | | | |
|---|---|---|---|---|---|
| MVHFVRCIQN | KIPHALPMSS | CVVFKSIYEF | KKMKQKITFV | MILIIALTGC | 50 |
| ASLTGPKKPP | RCNGKVTRAL | NRDKWDWDNK | NLILQEKNVK | PVRTPIILNT | 100 |
| LENEKATATV | TLKENSLNSI | TRETLPENTM | EIAREN | | 136 |

RECOMBINANT 15-KDA POLYPEPTIDE AND USE OF SAME IN DETECTING HUMAN INFECTION WITH *BARTONELLA HENSELAE*

CROSS-REFERENCE TO RELATED APPLICATION

The present application claims the benefit under 35 U.S.C. §1.119(e) of priority to U.S. Provisional Application No. 61/189,803 filed Aug. 22, 2008, the entire disclosure of which is hereby incorporated by reference in its entirety.

FIELD OF THE INVENTION

The present invention relates generally to the field of diagnostic assays for the detection of infectious agents in animals, including humans. Particular embodiments disclosed herein encompass novel recombinant fragments and synthetic polypeptides of 15-kDa protein that can be employed in the detection of *Bartonella henselae*.

BACKGROUND

*Bartonella henselae* is an intra-erythrocytic gram-negative bacterium and a causative agent for cat scratch disease in human. An estimated 28% of domestic cats are chronically infected with *Bartonella henselae*. Infected cats transmit the Bartonella bacteria to people from cat scratches or bites. The disease typically manifests as a regional lymphadenopathy, with some patients presenting with cutaneous lesions at the scratch sites. While cat scratch disease in most healthy individuals is self-limiting, approximately 10% of the patients may develop bacillary angiomatosis, bacillary peliosis, recurrent bacteriemia, and infective endocarditis. (See, e.g., Rochalimaea N., et al., New England Journal of Medicine, 1994, 330: pp. 1509-1515).

Young children and individuals with weakened immune systems are vulnerable to the Bartonella infection. In HIV-1 patients, *Bartonella henselae* can cause bacillary angiomatosis or peliosis hepatis which may include visceral involvement (Fournier, P. E., and D. Raoult. 1998. Cat scratch disease and an overview of other *Bartonella henselae* related infections, p. 32-62).

Several diagnostic assays for *Bartonella* infection are presently available. These include: (i) culturing, (ii) immunofluorescence assay ("IFA"), and (iii) polymerase chain reaction ("PCR") technologies. Culturing of *Bartonella* bacteria from blood samples is proven to be tedious and requires an extensive period (i.e., weeks), thus making this assay sub-optimal. Because of varying experimental culture conditions, it adversely affects the reproducibility of the methodology. IFA is not a quantitative assay, and does not provide useful information relating to sensitivity and specificity. In addition, IFAs for *Bartonella* bacterium have technical issues with cross-reactivity with other human pathogens (e.g., *Coxiella burnetii, Rickettsia rickettsii, Ehrlichia chaffeensis*, and *Treponema pallidum*) (Cooper, M. D., M. R. Hollingdale, J. W. Vinson, and J. Costa. 1976. A passive hemagglutination test for diagnosis of trench fever due to Rochalimaea quintana. *J. Infect. Dis.* 134:605-9). Moreover, IFAs are prone to subjective interpretations by individual technicians. Finally, IFAs are time-consuming and require expensive equipment such as fluorescent microscopes.

PCR technology utilizes the 16S rRNA gene in Bartonella bacterium to detect the presence of the pathogen. PCR has the advantage of simultaneous detection of DNA from multiple Bartonella species (e.g., *Bartonella henselae, Bartonella quintana, Bartonella bacilliformis, Bartonella elizabethae*, and *Bartonella clarridgeiae*). The problem with PCR is that it requires the presence of either the organism or its DNA in the test samples at the time of the assay in order to allow species-specific identification. Because of this limitation, PCR assay is only useful during the early stage of infection.

Detection of antigens represents an alternative method of detecting *Bartonella henselae*. For example, ELISA represents a quantitative detection assay that can provide good sensitivity and specificity. Unfortunately, there are only a limited number of antigens from *Bartonella* bacterium that have been shown to be useful for serological detection of *Bartonella*. Loa et al. reported the use of 17-kDa protein from *Bartonella* in the development of an ELISA (Loa et al., 2007). There is a continuing need for identification of novel Bartonella bacterium antigens useful in serological detection. The present inventors have addressed this deficiency of the prior art and have successfully cloned a gene from *Bartonella henselae* and expressed the corresponding polypeptide. The present inventors discovered that a 15-kDa polypeptide that is extremely useful in providing an immunoassay to detect the presence of antibodies to *Bartonella henselae* in patient's sera. The present disclosed antigen is novel and provides an improved clinical diagnostic tool in the field of *Bartonella* infection.

BRIEF SUMMARY OF THE INVENTION

The present invention is directed to the cloning and expression of the isolated virB7 gene in *Bartonella* to provide a recombinant protein of a molecular weight of 15-kDa. The present inventors discovered that the 15-kDa protein is useful in an ELISA assay in diagnostic tests for detecting *Bartonella henselae*.

In one aspect, the present invention provides a recombinant 15-kDa polypeptide. In another aspect, the 15-kDa protein has an amino acid sequence as set forth in SEQ ID NO: 2.

In another aspect, the present invention provides a composition comprising a recombinant polypeptide having an amino acid sequence as set forth in SEQ ID NO: 2 and a support. The support may be a microtiter well, polyethylene, polypropylene, or glass.

The present invention also provides for an isolated polynucleotide encoding the 15-kDa polypeptide of the present invention. In one aspect, the present invention provides an isolated polynucleotide encoding a polypeptide as set forth in SEQ ID NO: 2.

In another aspect, the present invention provides an isolated polynucleotide having a nucleotide sequence as set forth in SEQ ID NO: 1.

In another aspect, the present invention provides an expression vector comprising the isolated polynucleotide of the invention, operably linked to one or more expression control sequences. In an embodiment, the expression control sequences comprise a lac promoter. In another embodiment, the vector is an expression vector in *E. coli*.

The present invention also provides for a recombinant host cell containing the isolated polynucleotide and vector of the present invention.

In another aspect, the invention provides a method of preparing the recombinant polypeptide of the present invention, which comprises the steps of (a) introducing an isolated polynucleotide into a host cell, said isolated polynucleotide having a nucleotide sequence as set forth in SEQ ID NO: 1; (b) growing said host cell in a culture under suitable conditions to permit production of said recombinant polypeptide; and (c) isolating said recombinant polypeptide.

In another aspect, the present invention provides a method of detecting the presence of an antibody against *Bartonella henselae* in a biological sample of a mammal, comprising the steps of: (a) immobilizing a recombinant polypeptide of the present invention onto a surface; (b) contacting said recombinant polypeptide with a biological sample under conditions that allow formation of an antibody-antigen complex; and (c) detecting the formation of said antibody-antigen complex, wherein the presence of said antibody-antigen complex is indicative of the presence of said antibody against *Bartonella henselae* in said biological sample.

In another aspect, the present invention provides a method of diagnosing an infection of *Bartonella henselae* in a mammal, comprising the steps of: (a) obtaining a biological sample from a mammal suspected of having a *Bartonella henselae* infection; (b) immobilizing a recombinant polypeptide of the current invention onto a surface; (c) contacting said recombinant polypeptide with said biological sample, under conditions that allow formation of antibody-antigen complex; and (d) detecting said antibody-antigen complex, wherein said detected antibody-antigen complex is indicative of the presence of the antibody against *Bartonella henselae* in said biological sample.

In yet another aspect, the present invention provides an article of manufacture or a kit comprising a recombinant polypeptide of the present invention, and an instruction indicating the use of said recombinant polypeptide in detecting the presence of an antibody against *Bartonella henselae*.

BRIEF DESCRIPTION OF THE DRAWINGS

FIG. 2 depicts the nucleotide sequence of the full-length 15-kDa gene (SEQ ID NO: 1) in *Bartonella henselae*, previously deposited into the NCBI GenBank (GeneID: 2865504).

FIG. 3 depicts the amino acid sequence of the 15-kDa polypeptide (SEQ ID NO: 2) in *Bartonella henselae*, previously deposited into the NCBI GenBank (Accession #YP_034056).

DETAILED DESCRIPTION OF THE INVENTION

Figure 1:
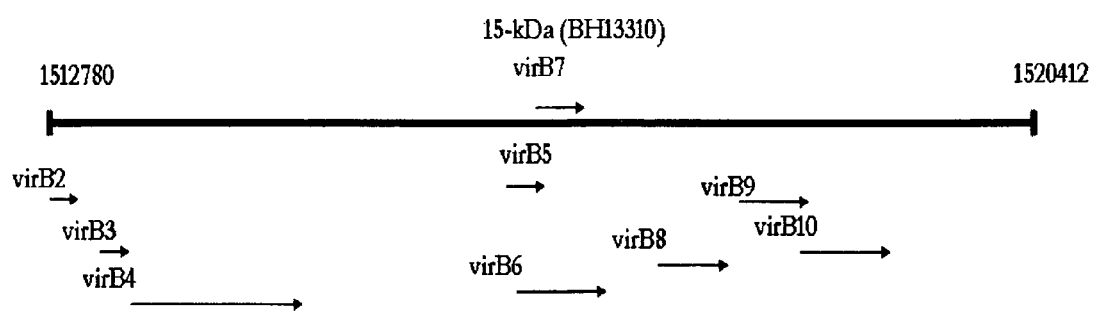
FIG. 1 depicts the genomic organization of *Bartonella henselae* virB operon. Open reading frames of various virulence proteins are represented by arrows. The gene (locus tag BH13310) encoding *Bartonella henselae* 15-kDa antigen is present in the virB7 operon.

The present invention can be better understood from the following description of preferred embodiments, taken in conjunction with the accompanying drawings. It should be apparent to those skilled in the art that the described embodiments of the present invention provided herein are merely exemplary and illustrative and not limiting. Numerous embodiments of the modifications thereof are contemplated as falling within the scope of the present invention and equivalents thereto. All publications, patent applications, patents, and other references mentioned herein are incorporated by reference in their entirety.

Definitions

As used herein the term "15-kDa" refers to a polypeptide having amino acid sequence as set forth in SEQ ID NO: 2. The polypeptide represents the virB7 protein (one of the 12 proteins in Type IV Secretory Protein System) in *Bartonella henselae*. The 15-kDa polypeptide is shown by the present inventors to bind to antibodies that are present in *Bartonella* patients' sera in an ELISA assay. For purposes of the present invention, the 15-kDa is intended to encompass some variations insofar as they possess the ability to interact with *Bartonella* patients' sera in an ELISA assay. One of ordinary skill in the art would appreciate that the amino acid sequence variations may include conservative substitutions or deletion of the amino acids. It would be further appreciated that polypeptides with 99% or 95% identity may possess the binding ability and is therefore encompassed by the present invention.

As used herein, the term "isolated" (when used in the context of polypeptides and nucleic acids) means that the polypeptides or nucleic acids are essentially free of other substances with which they may be found in vivo. In particular, the polypeptides or nucleic acid are substantially pure so as to be useful in, for example, generating antibodies, expression or producing pharmaceutical preparations.

As used herein, the term "control sequence" refers to DNA sequences necessary for the expression of an operably linked coding sequence in a host micro-organism. The control sequences that are suitable for prokaryotes, for example, include a promoter, optionally an operator sequence, and a ribosome binding site. Eukaryotic cells are known to utilize promoters, polyadenylation signals, and enhancers.

As used herein, the term "host cell" refers to a cell containing a vector and supports the replication and expression of the vector. Host cells may be prokaryotic cells such as *E. coli* or eukaryotic cells such as yeast, or mammalian cells. Preferably, host cell is *E. coli*.

As used herein, the term "introduced" refers to inserting a nucleic acid into a cell, which encompasses "transfection," "transformation," or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

As used herein, the term "ELISA" refers to "Enzyme-Linked ImmunoSorbent Assay" and is a biochemical technique used in detecting the presence of antibody or antigen in a sample.

As used herein, the term "mammal" refers to any vertebrate of the class mammalia, having the body more or less covered with hair, nourishing the young with milk from the mammary glands, and, with the exception of the egg-laying monotremes, giving birth to live young. Preferably, the mammal is human.

As used herein, the term "% amino acid sequence identity" is defined as the percentage of amino acid residues that are identical to the amino acid residues in the 15-kDa polypeptide. Alignment for purposes of determining percent amino acid sequence identity can be achieved in various ways that are well within the skill in the art, for instance, using publicly available computer software such as BLAST, BLAST-2, ALIGN or Megalign (DNASTAR) software.

As used herein, the terms "polypeptide," "peptide," or "protein" are used interchangeably.

As used herein, the term "operably linked" includes reference to a functional linkage between a promoter and a second sequence wherein the promoter sequence initiates and mediates transcription of the DNA sequence corresponding to the second sequence. Generally, "operably linked" means that the nucleic acid sequences being linked are contiguous and, where necessary to join two protein coding regions, contiguous and in the same reading frame.

As used herein, the term "promoter" includes reference to a region of DNA upstream from the start of transcription and involved in recognition and binding of RNA polymerase and other proteins to initiate transcription.

As used herein, the term "recombinant" includes reference to a cell or vector that has been modified by the introduction of a heterologous nucleic acid or that the cell is derived from a cell so modified.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium, or just a single time per host as the host reproduces by mitosis. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

15-kDa Polypeptide of *Bartonella henselae*

The present invention includes an isolated 15-kDa polypeptide having an amino acid sequence set forth in SEQ ID NO: 2. In *Bartonella henselae*, the virB operon is known to contain, among others, the virB7 gene which encodes a 15-kDa polypeptide (Alsmark et al., 2004).

In one embodiment, the present invention provides 15-kDa polypeptide variants insofar as they interact with antibody present in sera obtained from *Bartonella* infected patients. The polypeptides of the invention may be altered in various ways including amino acid substitutions, deletions, truncations, and insertions. Methods for such manipulations are generally known in the art. For example, amino acid sequence variants can be prepared by mutations in the DNA. Methods for mutagenesis and nucleotide sequence alterations are well known in the art. The present invention is intended to encompass conservative substitutions, such as exchanging one amino acid with another without altering the binding properties against antibody present in sera obtained from Bartonella infected patients.

It is intended that polypeptide having >95% and >99% amino acid identity to the 15-kDa polypeptides are encompassed by the present invention.

In one embodiment, the present invention provides an isolated polynucleotide that encodes a polypeptide having an amino acid sequence set forth in SEQ ID NO: 2.

The present invention provides an isolated nucleic acid molecule having nucleotide sequence set forth in SEQ ID NO: 1. In one embodiment, the present invention includes isolated nucleic acids that are variants of the nucleic acid residues set forth in SEQ ID NO: 1. In another embodiment, the variants include nucleic acid residues that contain degenerate codes.

The present inventors have discovered that the 15-kDa polypeptide serves as an antigen which is hypothesized to elicit a specific immune response in a mammal. Thus in mammals which have been infected with *Bartonella hensalae*, an immune response is elicited against the 15-kDa polypeptide.

In one embodiment, the present invention includes polynucleotides of the present invention which constitute an antigen having a specific binding activity towards antibodies present in sero-positive patients suffering from infection with *Bartonella henselae*.

In one embodiment, the antigens have specific binding activity towards IgG or IgM isotype present in sero-positive patients suffering from infection with *Bartonella henselae*.

Selection of a Replicable Vector

The nucleic acid (e.g., genomic DNA) encoding 15-kDa of the present invention may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

A number of promoters can be used in the practice of the invention. In one embodiment, a promoter can be employed which will direct expression of a polynucleotide of the present invention in *E. coli*. Other equivalent transcription promoters from various sources are known to those of skill in the art.

The 15-kDa may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the 15-kDa-encoding DNA that is inserted into the vector. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

Examples of suitable selectable markers for mammalian cells include those that enable the identification of cells competent to take up the 15-kDa-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 (Stinchcomb et al., *Nature*, 282:39 (1979); Kingsman et al., *Gene*, 7:141 (1979); Tschemper et al., *Gene*, 10:157 (1980)). The trp1 gene provides a selection marker for a mutant strain of yeast lacking the ability to grow in tryptophan, for example, ATCC No. 44076 or PEP4-1 (Jones, *Genetics*, 85:12 (1977)).

Expression and cloning vectors usually contain a promoter operably linked to the 15-kDa-encoding nucleic acid sequence to direct mRNA synthesis. Promoters recognized by a variety of potential host cells are well known. Promoters suitable for use with prokaryotic hosts include the β-lactamase and lactose promoter systems (Chang et al., Nature, 275:615 (1978); Goeddel et al., *Nature*, 281:544 (1979)), alkaline phosphatase, a tryptophan (trp) promoter system (Goeddel, *Nucleic Acids Res.*, 8:4057 (1980); EP 36,776), and hybrid promoters such as the tac promoter (deBoer et al., *Proc. Natl. Acad. Sci. USA*, 80:21-25 (1983)). Promoters for use in bacterial systems also will contain a Shine-Dalgarno (S.D.) sequence operably linked to the DNA encoding 15-kDa.

Transcription of a DNA encoding the 15-kDa by higher eukaryotes may be increased by inserting an enhancer sequence into the vector. Enhancers are cis-acting elements of DNA, usually about from 10 to 300 bp, that can act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the 15-kDa coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding 15-kDa.

Selection and Transformation of Host Cells

Host cells are transfected or transformed with expression or cloning vectors described herein for 15-kDa production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991).

Methods of eukaryotic cell transfection and prokaryotic cell transformation are known to the ordinarily skilled artisan, for example, $CaCl_2$, $Ca_2PO_4$, liposome-mediated and electroporation. Depending on the host cell used, transformation is performed using standard techniques appropriate to such cells. The calcium treatment employing calcium chloride, as described in Sambrook et al., or electroporation is generally used for prokaryotes. For mammalian cells without such cell walls, the calcium phosphate precipitation method of Graham and van der Eb, *Virology*, 52:456-457 (1978) can be employed. Transformations into yeast are typically carried out according to the method of Van Solingen et al., *J. Bact.*, 130:946 (1977) and Hsiao et al., *Proc. Natl. Acad. Sci.* (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, See Keown et al., Methods in Enzymology, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and KS 772 (ATCC 53,635). Other suitable prokaryotic host cells include Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. These examples are illustrative rather than limiting.

Glucose and IPTG Increase Protein Expression in Bacterial Cell Cultures

Addition of isopropyl-β-D-thiogalactopyranoside (IPTG) to bacterial cultures is a long-standing way to induce expression of plasmid-based genes for the production of recombinant proteins under the control of the lac promoter. IPTG binds to the lac repressor in *Escherichia coli*, thereby preventing binding of the repressor protein to DNA and blocking gene transcription.

Recombinant 15-kDa protein was expressed in *E. coli* using the IPTG induction method. A low level of protein expression was obtained when cell cultures were grown in cell medial (e.g., LB) containing IPTG. Surprisingly, the addition of glucose prior to IPTG induction dramatically increased protein expression levels. Although not to be bound by any theory, the present inventors believe that 15-kDa protein expression reaches a expression level where it becomes toxic to the cells. Addition of glucose is able to increase localization of 15-kDa into inclusion bodies, thereby protecting cells from toxicity.

In one embodiment, the present invention involves increasing protein expression levels in a bacterial cell culture by adding glucose prior to IPTG induction. In another embodiment, glucose is added in a range of about between 5 mg/mL-10 mg/ML, and more preferably in a range of about 8 mg/mL to 10 mg/ML.

In one embodiment, the present invention provides a method of localizing protein expression to an insoluble fraction of the cells by adding glucose prior to IPTG induction. In another embodiment, glucose is added in a range of about between 5 mg/mL-10 mg/ML, and more preferably in a range of about 8 mg/mL to 10 mg/ML.

Detecting Gene Amplification/Expression

Gene amplification and/or expression may be measured in a sample directly, for example, by conventional Southern blotting, Northern blotting to quantitate the transcription of mRNA (Thomas, *Proc. Natl. Acad. Sci. USA*, 77:5201-5205 (1980)), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence 15-kDa polypeptide or against a synthetic peptide based on the DNA sequences provided herein or against exogenous sequence fused to 15-kDa DNA and encoding a specific antibody epitope.

Purification of Recombinant 15-kDa Polypeptide

After expression, recombinant 15-kDa may be recovered from culture medium or from host cell lysates. If membrane-bound, it can be released from the membrane using a suitable detergent solution (e.g. Triton-X 100) or by enzymatic cleavage. Cells employed in expression of 15-kDa can be disrupted by various physical or chemical means, such as freeze-thaw cycling, sonication, mechanical disruption, or cell lysing agents.

It may be desired to purify 15-kDa from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the 15-kDa. Various methods of protein purification may be employed and such methods are known in the art and described for example in Deutscher, *Methods in Enzymology,* 182 (1990); Scopes, Protein Purification: Principles and Practice, Springer-Verlag, New York (1982). The purification step(s) selected will depend, for example, on the nature of the production process used and the particular 15-kDa produced.

Methods of Detecting and Diagnosing *Bartonella henselae* Using 15-kDa Polypeptide The present invention provides a method of detecting *Bartonella henselae* using isolated nucleotides and the 15-KDa polypeptide as described above. The invention also includes diagnosing an *Bartonella henselae* in a mammal which comprises detecting the presence or absence or a 15-kDa in a test sample of tissue cells obtained from said mammal, wherein the presence or absence of the 15-kDa in said test sample is indicative of the presence of *Bartonella henselae* in said mammal.

In one embodiment, the present invention uses immunoassays such as ELISA to detect 15-kDa and thereby diagnose the presence or absence of *Bartonella henselae*. In one embodiment, a sample of serum, urine, or uterine secretion may be obtained from a patient and may be contacted with a 15-kDa polypeptide of the present invention. Binding of the antibody to 15-kDa may be detected by any of the standard means known in the art. The 15-kDa may, for example, be immobilized on a substrate, contacted with the sample to allow binding of the antibodies to the epitope, and then washed to remove unbound materials. The presence of bound protein may then be assayed by standard means.

In another embodiment, a sample of serum, urine, or uterine secretion may be obtained from a patient and may be contacted with an anti-15-kDa antibody. Binding of the antibody to 15-kDa may be detected by any of the standard means known in the art. Antibodies to a 15-kDa epitope may, for example, be immobilized on a substrate, contacted with the sample to allow binding of the antibodies to the epitope, and then washed to remove unbound materials. The presence of bound protein may then be assayed by standard means. Alternatively, the assay may be of the "sandwich" type in which a first set of 15-kDa antibodies is first contacted with the sample and then washed, and then labeled antibodies to a second 15-kDa epitope are added. Binding of the second set of antibodies indicates the presence of 15-kDa bound to the first set. The labels used may be of any variety known in the art (e.g., enzymatic, radioactive, bioluminescent). Other antibody tests, including competitive binding tests, will be apparent to one of ordinary skill in the art.

In another embodiment, the present invention concerns an immune-related disease article of manufacture or diagnostic kit, comprising a 15-kDa polypeptide of the present invention or an anti-15-kDa antibody and a carrier in suitable packaging. The kit preferably contains instructions for using the 15-kDa polypeptide or antibody to detect the presence of anti-15-kDa-antibodies or the 15-kDa polypeptide, respectively. Preferably the carrier is pharmaceutically acceptable.

Elisa Assays

Detection of presence of antibodies which specifically bind with *Bartonella henselae* can be analyzed by an ELISA assay. A *Bartonella henselae* antigen is first immobilized onto a surface. A biological sample (such as blood, plasma, or serum) is then added. Antibodies present in the biological sample are allowed to bind with the bound *Bartonella henselae* antigen. After washing, a secondary antibody bound to a detectable moiety can be added to enhance the detection. ELISA can be readily adapted to accomplish the detection of both *Bartonella henselae* antigen and antibodies which specifically bind therewith.

IgG ELISA may be performed as follows: (1) immobilizing a *Bartonella henselae* antigen onto a surface; (2) contacting the bound antigen with a biological sample containing antibodies from a mammal; (3) adding an anti-human IgG antibody that has a detectable moiety (e.g., horseradish peroxidase enzyme); (4) adding a substrate for the enzyme; (5) adding a color reagent. Color change is indicative of the presence of IgG antibodies.

IgM ELISA may be performed using the similar protocol as in IgG ELISA as described above (i.e., immobilizing the 15-kDa protein onto a surface).

Alternatively, IgM ELISA may also be performed via "antibody capture" as follows: (1) immobilizing an anti-human IgM antibody onto a surface; (2) contacting the bound antibody with a biological sample from a mammal; (3) contacting the above with biotinylated *Bartonella henselae* antigen (e.g., 15-kDa); (4) adding strepavidin-horseradish peroxidase; (5) adding a color reagent. Color change is indicative of the presence of IgM antibodies. In one embodiment, IgM capture ELISA is used. Specifically, flat-bottomed 96-well polystyrene plates are coated with goat anti-human IgM antibody, followed by serial two-fold dilutions of sera including 5 negative controls, biotinylated *Bartonella henselae* or negative control antigens, and strepavidin-horseadish peroxidase goat and the substrate (TMB). Between each step, plates are incubated for 1 hour at 37° C., and then washed 3 times with 0.05% Tween 20 in phosphate buffered-saline (pH 7.4). Dilutions of sera are considered positive when the difference in absorbance between that serum specimen when tested with *Bartonella henselae* antigen and the negative control antigen exceeds the mean plus 3 standard deviations of the 5 negative control sera tested with both *B. henselae* and negative control antigens. Both the IgG and IgM ELISA assays are effective for the diagnosis of cat scratch disease and bacillary angiomatosis.

The following examples are provided to further illustrate various preferred embodiments and techniques of the invention. It should be understood, however, that these examples do not limit the scope of the invention described in the claims. Many variations and modifications are intended to be encompassed within the spirit and scope of the invention.

EXAMPLES

Example 1

VirB7 (15-kDa) Gene and its Protein Product (15-kDa Protein) Genomic Location of virB7 (15-kDa) Gene In *Bartonella henselae*, the virB operon is known to contain, among others, virB7 gene which encodes a 15-10a polypeptide (Alsmark et al., 2004). The function of the virB7 gene product (i.e., 15-kDa) is largely unknown. It has been shown that the protein products of the virB7 gene and virB5 gene are physically associated. Both protein products belong to the Type IV Secretion System (TIVSS) in *Bartonella* (Shamaei-Tousi, 2004). FIG. 1 depicts the organization of the virB operon in *Bartonella henselae*.

15-kDa Polypeptide is a Predicted Membrane Protein Having a Single Transmembrane Domain To the best of the present inventors' knowledge, there is no public available information regarding the cellular location of the 15-kDa polypeptide. We used an in silico approach to predict the putative cellular location for this protein.

First, we took advantage of the experimental evidence in *Agrobacterium tumefaciens* (a plant pathogen) suggesting that virB7 is the functional homolog of 15-kDa in *Bartonella henselae* (Krall et al., 2002; Ward et al., 2002). According to the Krall's model, virB7 is a periplasmic protein anchored to the outer membrane. Notably, virB7 interacts with virB5 and virB9 within the TIVSS in *Bartonella henselae* (Krall et al., 2002; Ward et al., 2002).

Figure 4A:
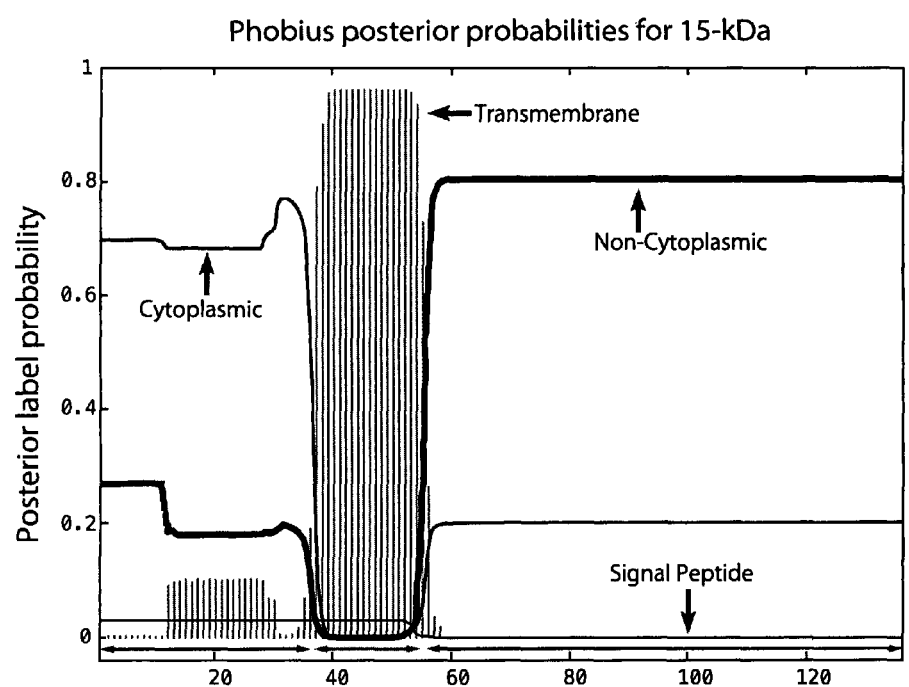
FIG. 4a depicts the transmembrane topology for the 15-kDa protein in *Bartonella henselae* using the Phobius online tool (http://phobius.sbc.su.se). According to this model, the 15-kDa protein contains a single transmembrane domain spanning the region from amino acid residues 37 to 55 of SEQ ID NO: 2.

Next, we used the TMHMM server 2.0 (A. Krogh et al, 2001, http://www.cbs.dtu.dk/services/TMHMM-2.0), and analyzed the number and location of potential transmembrane helices present within the 15-kDa protein (data not shown). Furthermore, we used the Phobius online tool (http://phobius.sbc.su.se), and analyzed the 15-kDa protein for the presence of transmembrane regions and the presence of a signal peptide. The Phobius tool is reported to have additional advantages over TMHMM program in that it significantly reduces the level of false transmembrane and signal peptide classifications (Sonnhammer et al., 2004). According to the Phobius model, we found that 15-kDa protein contains a single transmembrane domain spanning amino acid residues 37-55. We also observed from the Phobius model that the 15-kDa protein lacks a signal peptide. Our finding is summarized in FIG. 4a, which shows the probability plot of transmembrane helices in 15-kDa protein using the Phobius program.

Figure 4B:
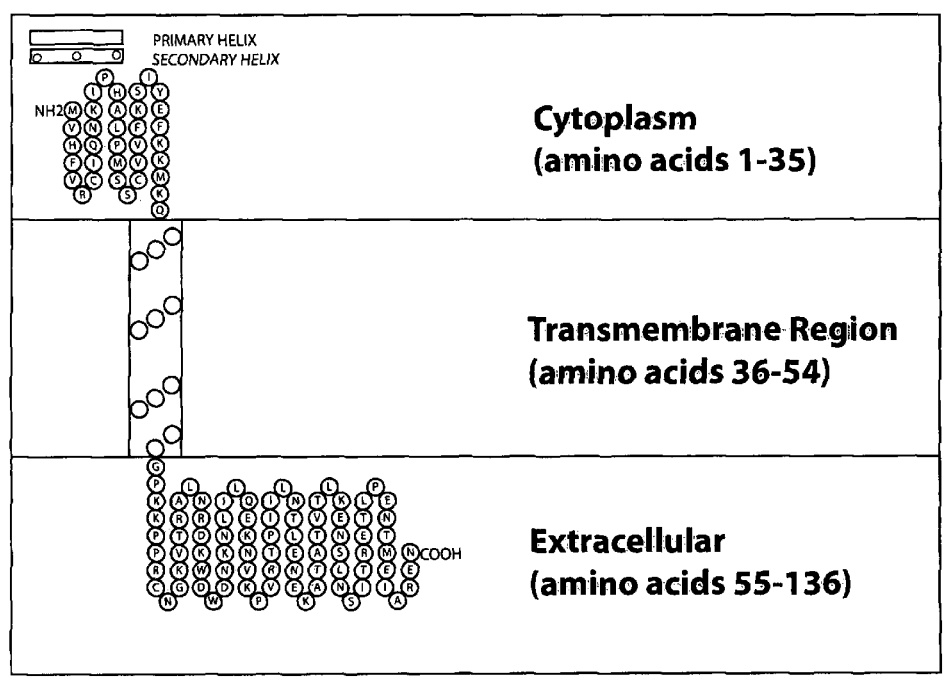
FIG. 4b depicts the predicted topology for the 15-kDa protein within the cellular membrane using the SOSUI (classification and secondary structure prediction system for membrane proteins) online tool (http://bp.nuap.nagoya-u.ac.jp/sosui). According to this model, the predicted topology of the 15-kDa (virB7) protein indicates the presence of a single transmembrane helix spanning the region from residues 37-55 of SEQ ID NO: 2.

We also evaluated the topology of 15-kDa protein. To do so, we used the SOSUI (classification and secondary structure prediction system for membrane proteins) online tool (http://bp.nuap.nagoya-u.ac.jp/sosui). According to the SOSUI model, we found that 15-kDa contains a single transmembrane helix spanning amino acid residues 37-55. Our finding is summarized in FIG. 4b, which shows the predicted topology of virB7 (15-kDa) within the cell membrane.

In conclusion, both the Phobius and SOSUI models reveal the presence of a single transmembrane helix spanning the region from residues 37-55. Altogether, these in silico data provide convincing evidence that 15-kDa is a membrane-associated protein.

Example 2

Amplification and Sub-Cloning of the VirB7 (15-kD) Gene

We next determine if the 15-kDa protein from *Bartonella henselae* is a good antigen for immuno-detection. We addressed this question by expressing the recombinant 15-kDa protein and evaluated its usefulness as a good diagnostic marker for *Bartonella henselae*. In this study, we PCR amplified the 15-kDa gene encoding the entire ORF of the 15-kDa protein, and ligated the cloned gene into an expression vector.

PCR Amplication of the virB7 Gene

Genomic DNA nucleotide sequence of *Bartonella henselae* Houston strain-1 has been deposited in GenBank (accession number NC_005956). The nucleotide sequence for the virB7 (15-kDa) gene has been deposited in GenBank (GeneID: 2865504). The disclosures of the genomic DNA and virB7 (15-kDa) gene nucleotide sequences are incorporated herein in their entirety.

Genomic DNA of *Bartonella henselae* Houston strain-1 was purchased from American Type Culture Collection (ATCC 49882). We designed PCR primers for the amplification of the 15-kDa gene. The forward and reverse PCR primers included 5'LIC extensions to facilitate directional and in-frame cloning into the pET30 Ek/LIC vector (Novagen, Madison Wis.). The sequences of the forward and reverse primers were 5'-GACGACGACA AGATGTGCAT TTGTAAG-3' (SEQ ID NO: 3) and 5'-GAGGAGAAGC CCGGTTTAAT TTTCACG-3' (SEQ ID NO: 4), respectively.

Figure 5:
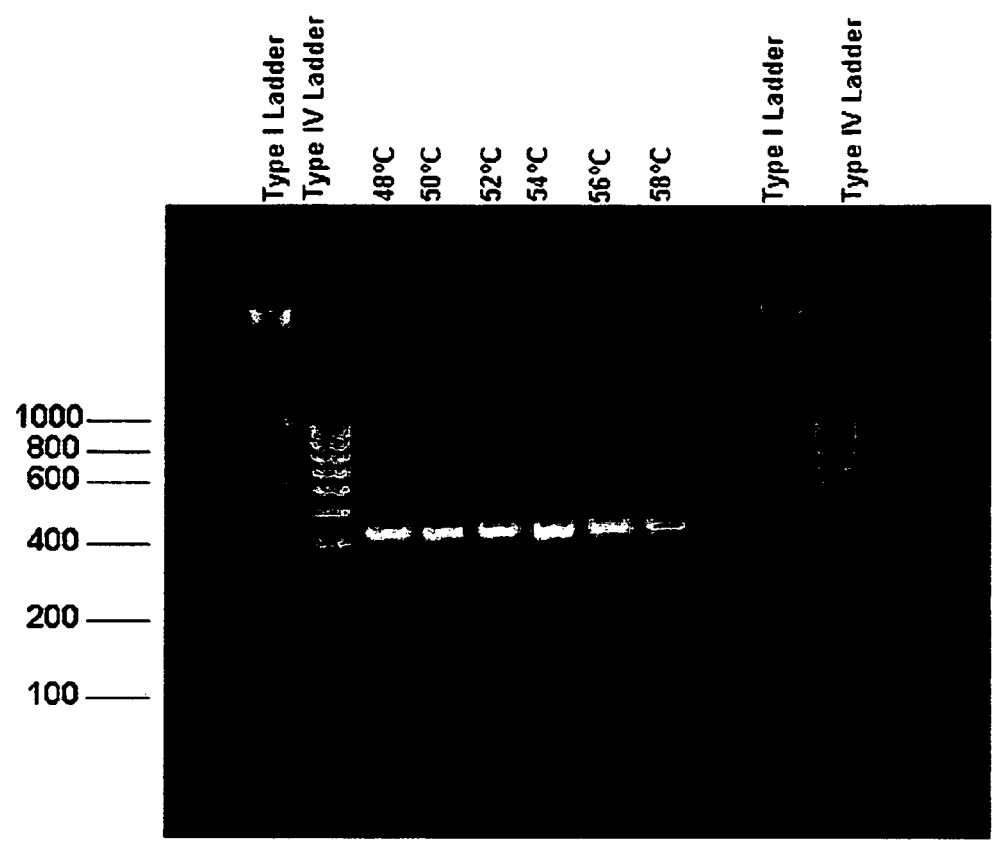
FIG. 5 illustrates PCR amplification of the 15-kDa gene from *Bartonella henselae* Houston strain-1 genomic DNA using a gradient PCR approach. A single amplicon of expected size (~411 bp) was observed on the agarose gel for each of the six different annealing temperatures.

Using these primers, we amplified the *Bartonella henselae* virB7 (15-kDa) by gradient PCR method. We performed the PCR reaction (condition details, see Experimental Protocol). At the completion of PCR, an aliquot of the reaction was analyzed by agarose gel electrophoresis to confirm the presence of an amplicon of expected size (~411 bp). The remainder of the PCR reaction was treated to remove excess primers and DNA polymerase in preparation for subcloning. We observed amplicons of expected size for each of the different annealing temperatures tested (see FIG. 5), indicating successful PCR amplification across the range of temperature tested.

T4 Polymerase Treatment of virB7 and Ligation to pET30 Vector

Figure 6:
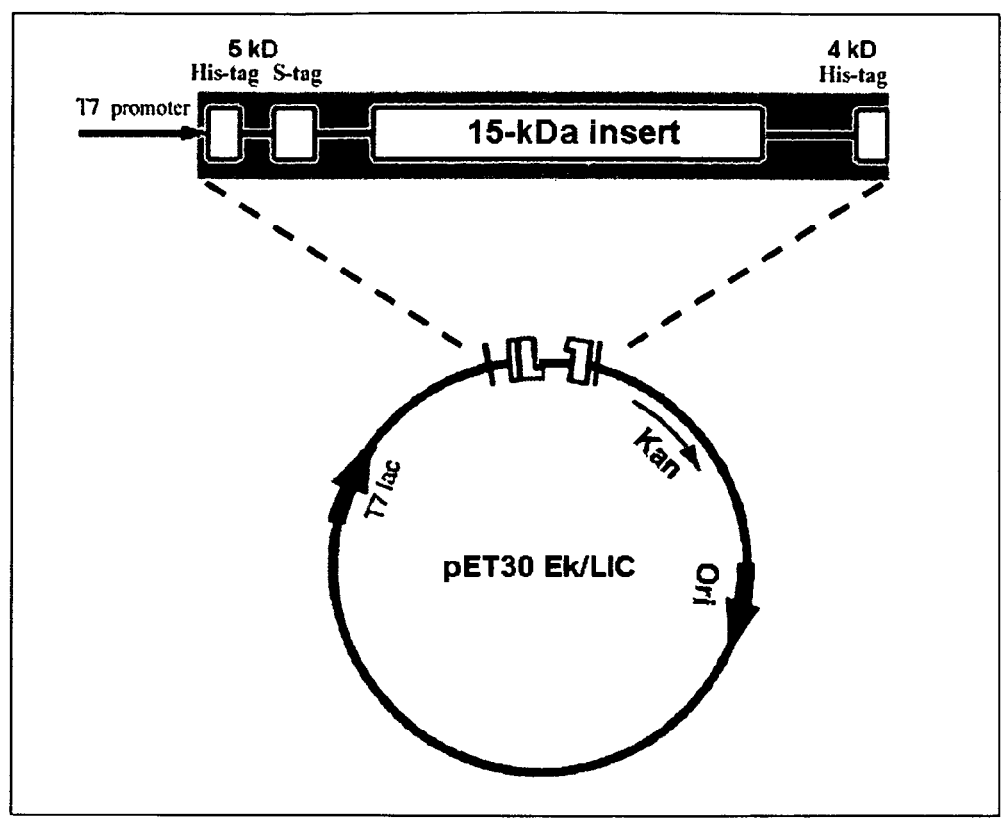
FIG. 6 is a schematic representation of the recombinant pET30 vector containing the 15-kDa gene in-frame of the T7 promoter and His-tag sequences.

We chose the amplicon from the 56° C. reaction for further analysis. In this study, we subcloned the amplicon into pET30 expression vector (Novagen). To do so, it is necessary to create compatible ends between the amplicon and the chosen vector (i.e., pET30 Ek/LIC). We generated overhangs compatible with the Ek/LIC cloning vector on the insert DNA by T4 DNA polymerase treatment of the PCR amplicon (see Experimental Protocol). We ligated the treated amplicon into the expression vector to form pET30/15-kDa. FIG. 6 depicts the pET30 vector containing the 15-kDa inserted gene.

Example 3

Expression of VirB7 Gene: Transformation of NovaBlue *E. coli*

In these series of experiments, we transformed the pET30/15-kDa insert into a host cell (NovaBlue *E. coli*). We chose NovaBlue *E. coli* because this cell is optimized for producing a stable cell line containing a recombinant insert. (See, Novagen EK/LIC manual). Heat-shock protocol for transformation was used (details, see Experimental Protocol). After transformation, cells were plated onto LB agar plates containing an antibiotic (kanamycin). Transformed cells were incubated at 37° C. overnight.

Example 4

Colony PCR of NovaBlue Transformants

Figure 7:
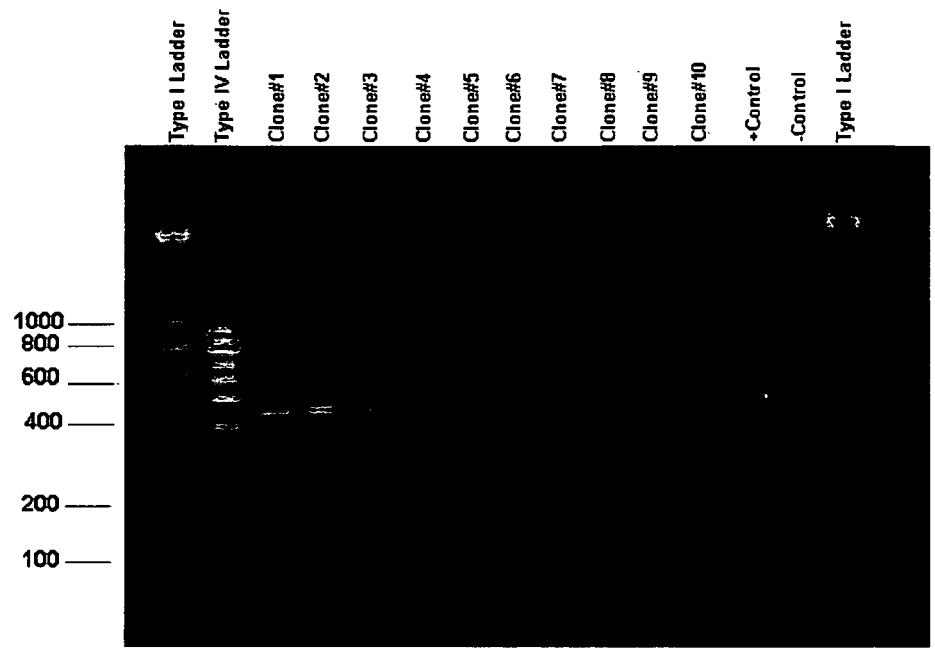
FIG. 7 illustrates PCR amplification of the recombinant 15-kDa gene in pET30 vector following transformation into NovaBlue *E. coli*. Ten colonies were randomly selected from NovaBlue *E. coli* grown on LB plates and amplified by PCR.

To confirm the presence of insert DNA (pET30/15-kDa) in transformed cells, we selected several colonies (i.e., 10 colonies) and performed colony PCR to confirm the presence of pET30/15-kDa in these colonies. Colony PCR was performed using the same set of Ek/LIC primers as in the amplification of the 15-kDa gene from the *Bartonella* genomic DNA (described in Example 1). As shown in FIG. 7, an amplicon of expected size (~411 bp) was observed following colony PCR analysis. NovaBlue *E. coli* colonies containing the pET30/15-kDa insert were then further cultured in LB-kanamycin broth (for the isolation of plasmids).

Example 5

Isolation of Recombinant Plasmids for Sequence Analysis

We chose colonies 1 and 2 (shown in the gel in FIG. 7) for further analysis. We picked colonies 1 and 2 and inoculated and cultured each colony separately into 5 mL LB broth with kanamycin. After overnight growth, we isolated plasmids from these cultures using the Wizard Plus SV miniprep DNA purification system. The concentration and quality ($OD_{260/80}$ nm) of plasmid DNA was determined using a spectrophotometer. The plasmid DNA was found to be of sufficient concentration and quality for sequence analysis.

Example 6

Sequencing of pET30/15-kDa Insert from Transformed NovaBlue E. coli

In this study, we sequenced the pET30/15-kDa insert in order to (i) confirm its identity and (ii) determine if the open reading frame is in-frame of the His-tag sequence. For sequencing, we used the two sets of primers. The first primer set was the same as that used for PCR amplification in Example 2. The second primer set contains the forward T7 promoter (5'-TAATACGACTCACTATAGGG-3') (SEQ ID NO: 5) and the reverse T7 terminator (5'-GCTAGTTAT-TGCTCAGCGG-3') (SEQ ID NO: 6) vector-specific primers. With the primer sets and the isolated pET30/15-kDa plasmids, we sequenced across the insert/vector junctions in both forward and reverse directions. Sequencing was performed using an Applied Biosystems 3130 Genetic Analyzer (HITACHI, Foster City, Calif.) sequencer.

With the sequences obtained from colony 1 and colony 2, we used BLAST (Basic Local Alignment Search Tool, http://blast.ncbi.nlm.nih.gov/Blast.cgi) analysis and found that the insert DNA (from colony 2) matched perfectly with the 15-kDa gene sequence deposited under GeneID: 2865504. Using the Lasergene 6 software (DNAStar) for sequence manipulation, we determined that the His-tag was in-frame of the open reading frame (ORF) (Accession #YP_034056).

Our sequence analysis confirms that both colony 1 and colony 2 contained the 15-kDa insert. Recombinant plasmid of colony 2 was chosen for further evaluation.

Example 7

Expression of VirB7 Gene: Transformation of BL21 (DE3) E. coli

We transformed the pET30/15-kDa plamid (obtained from colony 2) into BL21 (DE3) competent E. coli (Novagen). We chose BL21 (DE3) E. coli because this cell is optimized for protein expression. Heat shock transformation protocol (see Experimental Protocol) was used to transform the pET30/15-kDa plamid into competent BL21 (DE3) E. coli cells. The transformed cells were plated onto LB agar plates (with kanamycin), and incubated overnight at 37° C.

Example 8

Colony PCR of BL21 (DE3) Transformants

Figure 8:
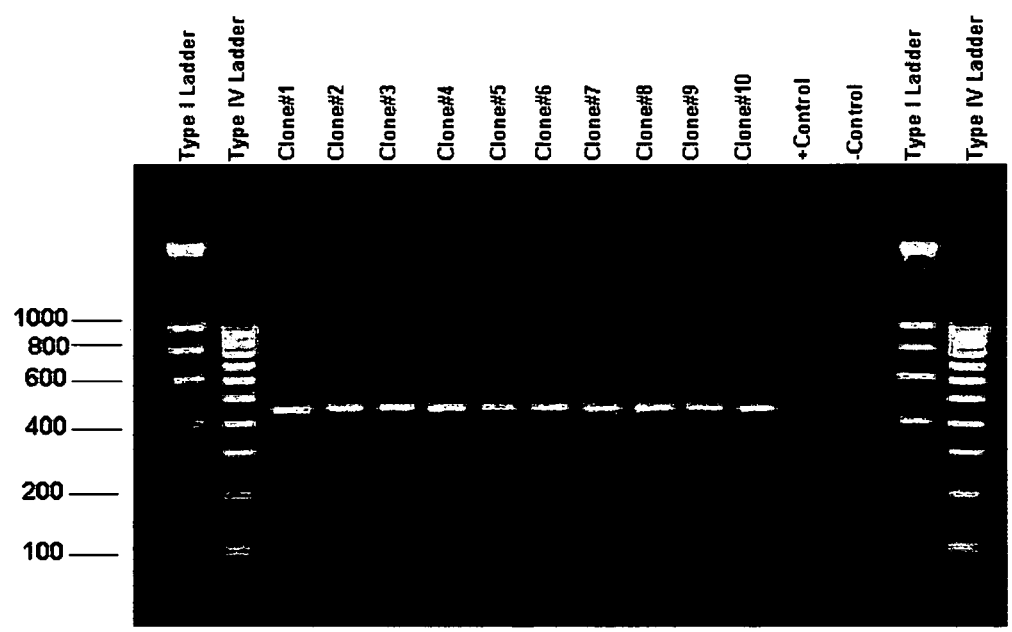
FIG. 8 illustrates PCR amplification of the recombinant 15-kDa gene in pET30 vector following transformation into BL21 (DE3) *E. coli*. Ten colonies were randomly selected from BL21 (DE3) *E. coli* grown on LB plates and amplified by PCR.

We confirmed the presence of insert DNA (pET30/15-kDa) in transformed cells. We selected 10 colonies and performed colony PCR amplification using the same set of Ek/LIC primers as in the amplification of the 15-kDa gene from the Bartonella genomic DNA (described in Example 1). As shown in FIG. 8, an amplicon of expected size (~411 bp) was observed on each of the ten (10) colonies. We made glycerol stocks for these colonies. For IPTG induction and expression studies, we used transformed cells from the glycerol stocks.

Example 9

Protein Expression of virB7 (15-kDa) in E. coli

Figure 9:
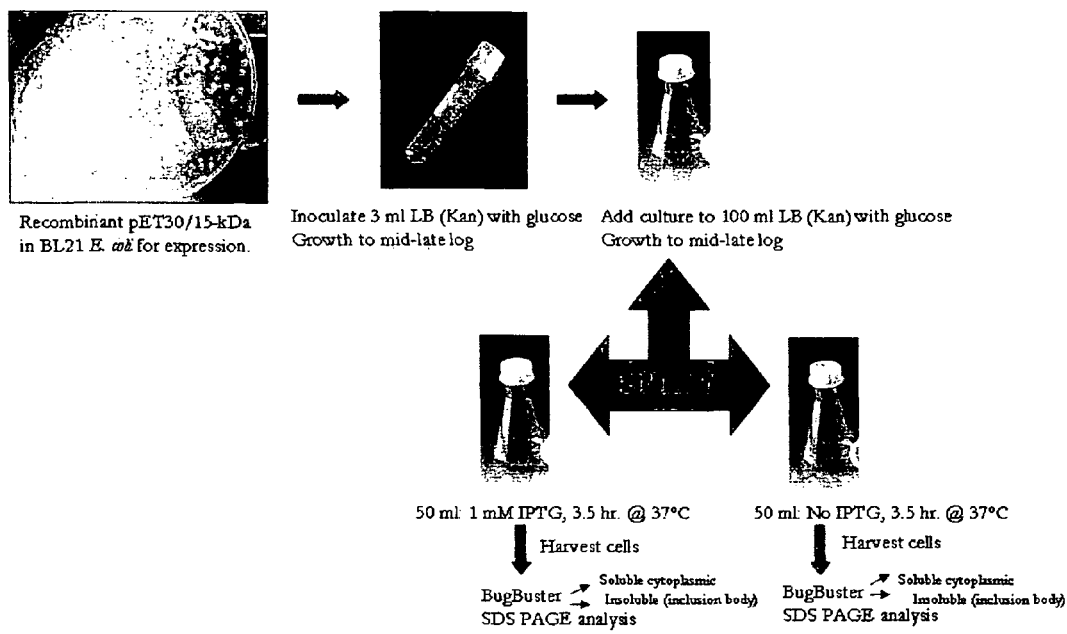
FIG. 9 illustrates the work-flow for IPTG induction and SDS-PAGE analysis of the recombinant 15-kDa protein.

We expressed the recombinant 15-kDa protein in BL21 (DE3) E. coli using IPTG induction method. The BL21 (DE3) E. coli transformants were induced with IPTG under the conditions detailed in Experimental Protocol section. In brief, transformant cultures were grown to mid-log ($OD_{600}$=0.5) at 37° C., followed by induction of protein expression by adding IPTG (1 mM). No IPTG was added in the negative control. Cultures were allowed to proceed for 3.5 hours at 37° C. FIG. 9 depicts the work-flow diagram for IPTG induction and analysis of recombinant 15-kDa. Cells were harvested after 3.5 hour-incubation and treated to obtain soluble and insoluble fractions, which were then analyzed by SDS-PAGE and Coomassie blue staining. We observed little, of any, protein expression when cultures were grown in LB containing IPTG (1 mM) (data not shown).

Example 10

Enhancement of Protein Expression of virB7 (15-kDa) in E. coli with Glucose

We consistently observed protein induction with IPTG (1 mM); and the induced 15-kDa protein typically obtained at a concentration of ~100 µg/ml. We made several attempts to increase the level of induced protein. We hypothesized that 15-kDa may be toxic to the E. coli cells, and thus led to sub-optimal protein expression.

We next examined whether glucose, by virtue of its purported ability to reduce the basal level of expression from recombinant plasmid, would alter the protein expression. The present inventors surprisingly discovered that addition of glucose in E. coli culture prior to IPTG enhances the protein expression of 15-kDa. We tested a range of glucose concentrations (5 mg/mL-10 mg/mL) and varying IPTG incubation times (2 hours-3.5 hours). Only small enhancement of 15-kDa expression was observed with 5 mg/mL glucose (data not shown). 15-kDa protein expression was significantly enhanced with 8 mg/mL and 10 mg/mL glucose. Using 8 mg/mL glucose, we observed enhanced 15-kDa protein expression over the entire IPTG incubation time period between 2-3.5 hours. (See, FIGS. 10 and 11)

Example 11

Soluble and Insoluble Fractions of Expressed 15-kDa Protein

In the absence of glucose, we observed the expressed 15-kDa protein to be localized exclusively in the soluble fraction and negligible level could be purified from the insoluble fraction (i.e., inclusion bodies) (data not shown).

Figure 12:
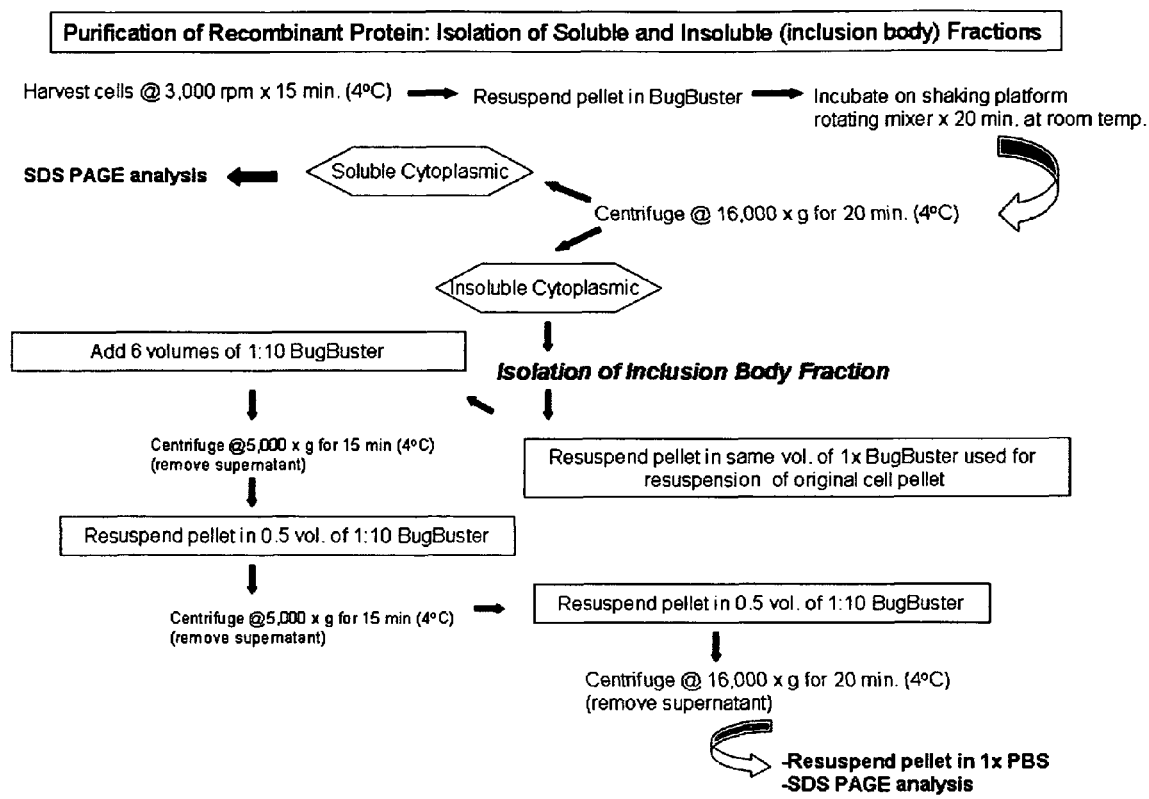
FIG. 12 is a flow chart depicting the purification protocol for soluble and insoluble (inclusion body) fractions of the *E. coli* cells expressing recombinant 15-kDa protein.

In sharp contrast, glucose enhanced expression of 15-kDa protein, and we observed that majority of the expressed protein is localized in the inclusion bodies. To purify the 15-kDa protein, E. coli cells were first lysed using BugBuster Master Mix (Novagen). FIG. 12 depicts the workflow for isolating the soluble fraction and the insoluble fraction as well as procedure in obtaining the inclusion bodies. A soluble fraction and an insoluble fraction were obtained.

Example 12

SDS-PAGE Analysis of Expressed 15-kDa Protein

Figure 10:
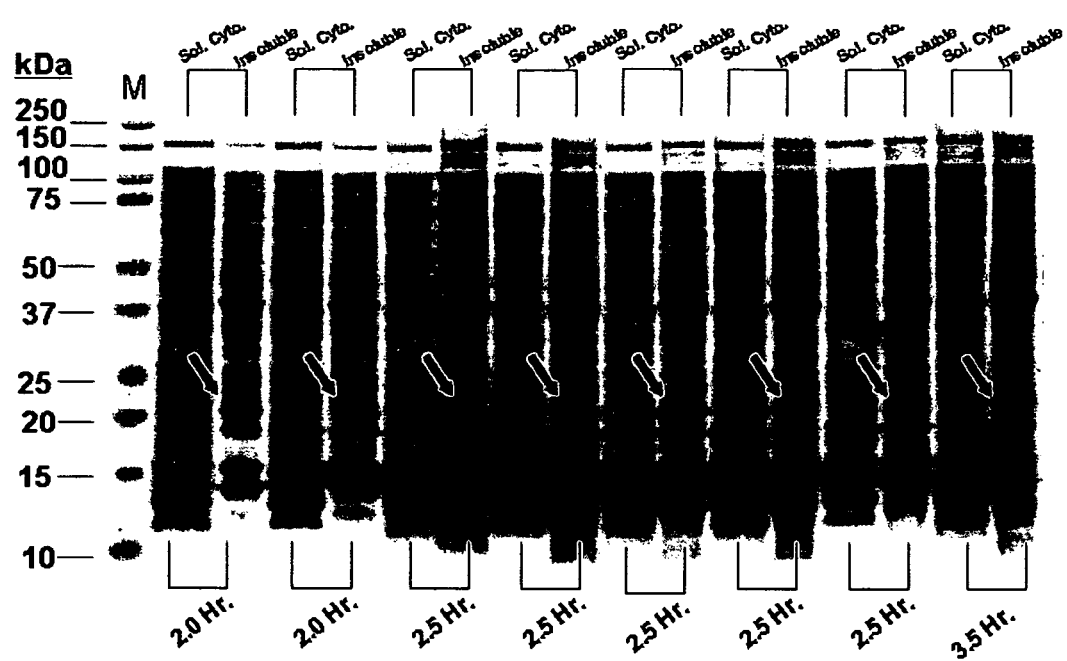
FIG. 10 depicts a Coomassie-blue stained SDS-PAGE gel of IPTG-induced 15-kDa protein. Recombinant 15-kDa in BL21 *E. coli* was grown in LB supplemented with glucose prior to the addition of IPTG as described in the text. Cells were incubated in LB with IPTG for the indicated times (2.0-3.5 hours). The arrows point to an induced protein band of expected size (~21-kDa).
Figure 11:
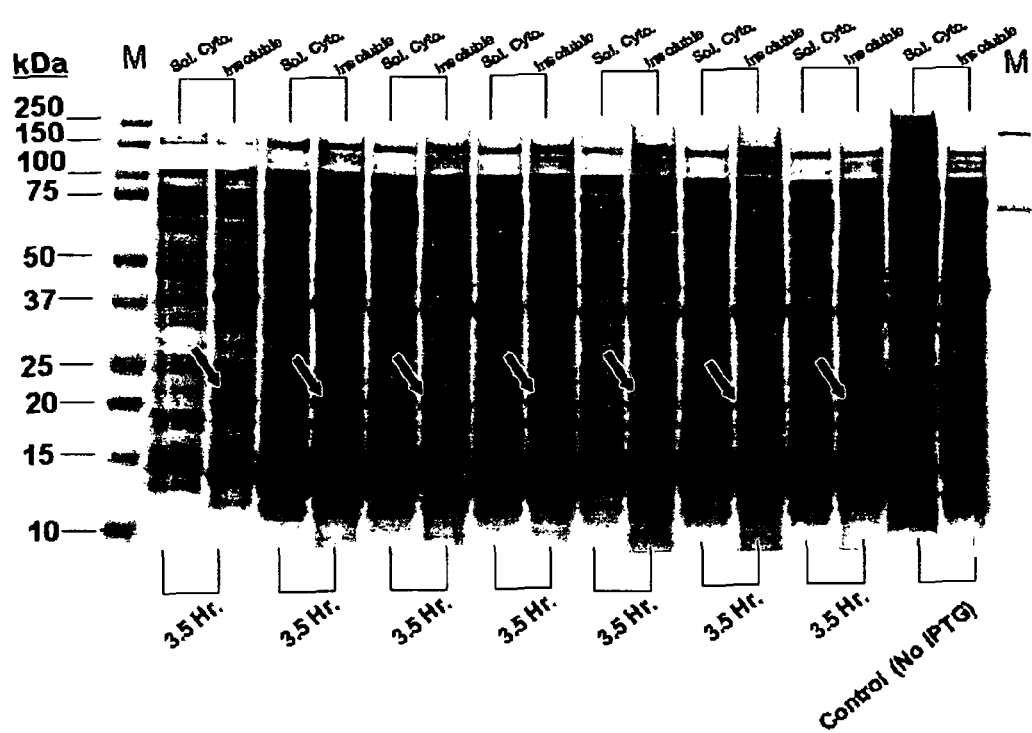
FIG. 11 depicts a Coomassie-blue stained SDS-PAGE gel of IPTG-induced 15-kDa protein. Recombinant 15-kDa in BL21 *E. coli* was grown in LB supplemented with glucose prior to the addition of IPTG as described in the text. Cells were incubated in LB with IPTG for the indicated time (3.5 hours). The arrows point to an induced protein band of expected size (~21-kDa). No induction is observed in the control lane (i.e., "No IPTG").

The SDS-PAGE Coomassie gels shown in FIGS. 10 and 11 indicate that the majority of the recombinant 15-kDa protein is present in the insoluble fraction (arrows). In this study, the E. coli cells were cultured in the LB growth media supplemented with glucose prior to IPTG induction. (See, FIGS. 10 and 11).

Example 13

Purification of Recombinantly Expressed 15-kDa Protein

We used Ni-NTA resin column to purify the expressed 15-kDa protein from the soluble and insoluble fractions. Purification was performed by adding soluble fraction over a Ni-NTA resin (nickel resin) column (Novagen, Madison, Wis.). We purified insoluble fraction under urea denaturing conditions as follows. First, the insoluble fraction was re-suspended in 4 ml lysis buffer. Then, 1 ml of Ni-NTA resin was added to the tube. The tube containing the resin/protein mixture was shaken on a rotating mixer for 1 hour at room temperature. At the end of 1 hour, the resin/protein mixture was emptied into a column, and fractions collected.

Figure 14:
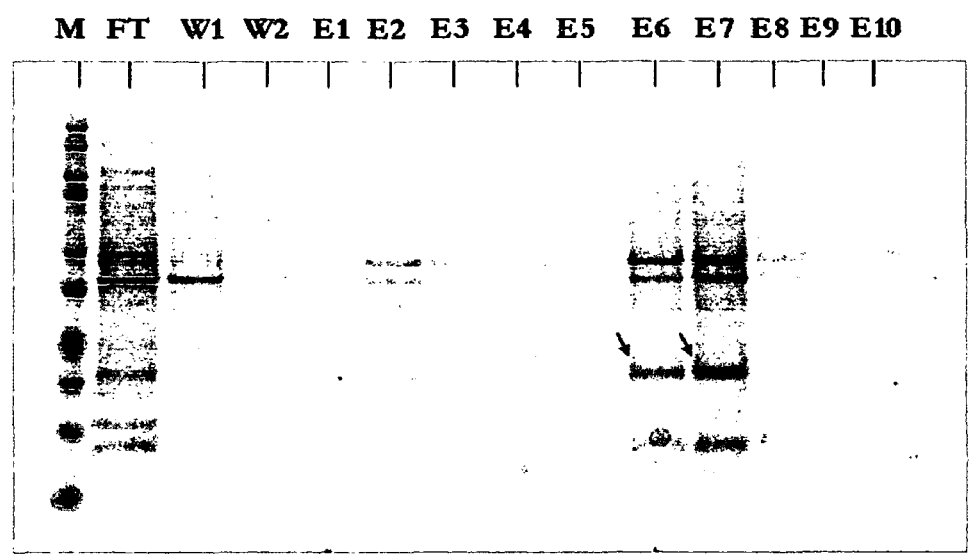
FIG. 14 depicts a Coomassie blue-stained SDS-PAGE gel showing the protein fractions obtained following nickel resin (Ni-NTA) purification of 15-kDa. Lysis denaturing buffer containing 15-kDa protein under urea denaturing conditions was eluted using Ni-NTA. FT=Flow-through, W1=Wash 1 (pH 6.3), W2=Wash 2 (pH 6.3), E1-E5=Elution 1-5, (pH 5.9), E6-E10=Elution 6-10, pH 4.5. Majority of the 15-kDa protein (shown by arrows in E6, E7) elutes in these two fractions.

FIG. 14 shows a coomassie blue-stained SDS gel of the protein fractions obtained following Ni-NTA purification of 15-kDa (in lysis denaturing buffer) under urea denaturing conditions. In our experience, a majority of the recombinant protein consistently elutes in fractions 6 and 7.

Figure 15:
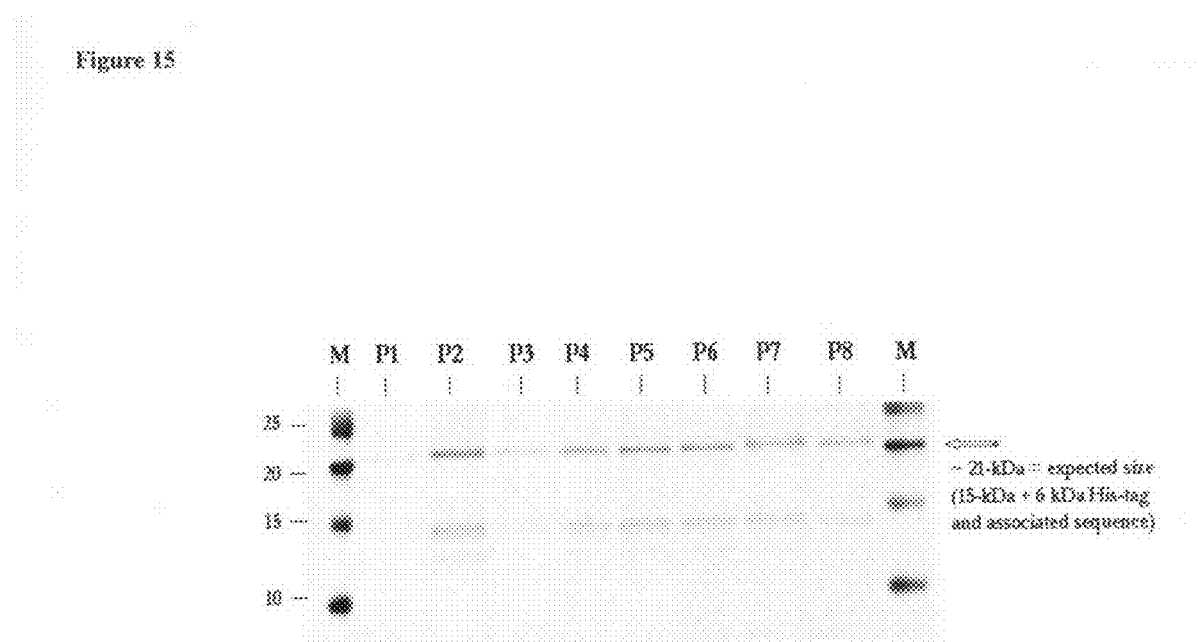
FIG. 15 depicts a Coomassie blue-stained SDS-PAGE gel showing eight separate preparations (P1-P8) of the recombinant 15-kDa protein. Elution fractions 6 and 7 from each of the eight preparations were combined into a single tube and analyzed by SDS-PAGE.

FIG. 15 shows a coomassie blue-stained gel of recombinant protein collected from combined fractions 6 and 7 from eight separate purification experiments (P1-P8).

Example 14

Figure 13:
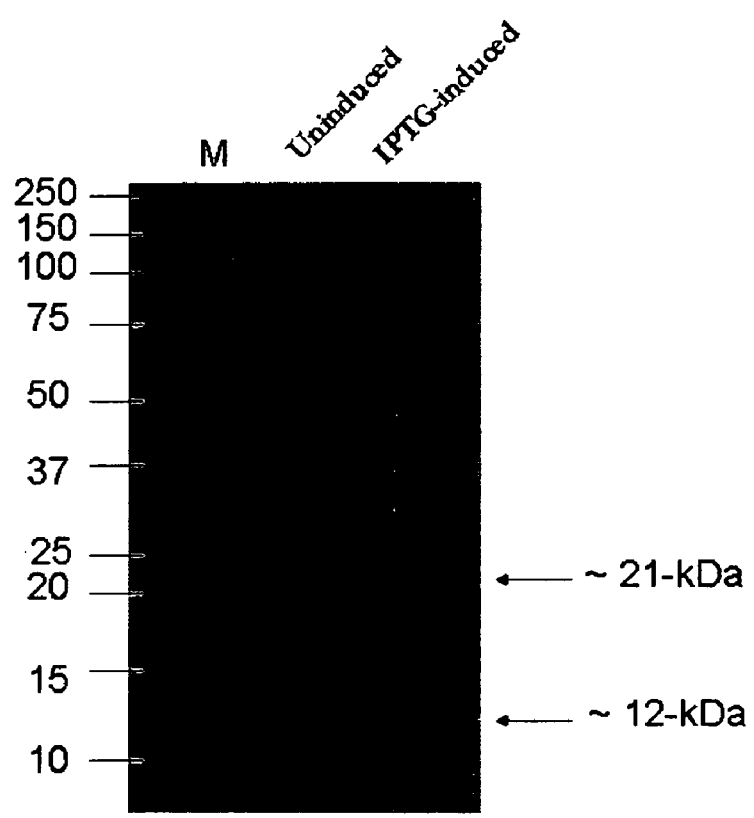
FIG. 13 depicts Western detection of the purified recombinant 15-kDa protein (semi-dry blotted onto nitrocellulose membrane) using a monoclonal antibody directed against the 6×His-tag. The antibody cross-reacts with a protein band of ~21-kDa (i.e.,15-kDa+6-kDa for 6×His-tag and associated sequences). The antibody also cross-reacts with a protein band of ~12-kDa.

Evaluation of the rVirB7 (r15-kDa) Antigen by Western Analysis Using a Monoclonal Anti-His Tag Antibody FIG. 13 shows the results of Western detection of purified recombinant I 5-kDa protein (semi-dry blotted onto nitrocellulose membrane) using a monoclonal antibody directed against the 6×His-tag. The antibody cross-reacts with a protein band off ~21-kDa (15-kDa+6-kDa for 6×His-tag and associated sequences).

We also noted that the antibody cross-reacts with another protein (i.e., ~12-kDa). (See, FIG. 13). Without bound by any theory, we speculate that the cross-reactive protein is a truncated form of 15-kDa lacking the c-terminal portion of the protein. When expressing recombinant proteins containing rare codons such as Arg (AGG, AGA, CGG, CGA), Gly (GGA), Ile(AUA), Leu(CUA), Pro (CCC), which are under-represented in the *E. coli* genome, truncated forms may occur. when the mRNA of heterologous target genes is overex-pressed in *E. coli*, differences in codon usage can impede translation due to the demand for one or more tRNAs that may be rare or lacking in the population. Hence, tRNA population closely reflects the codon bias of the mRNA population. (See, e.g., pET System Manual) (Novagen User Protocol TB055). Insufficient tRNA pools can lead to translational stalling, premature translation termination, translation frameshifting, and amino acid misincorporation.

To further test this hypothesis, we used the Graphical Codon Usage Analyzer 2.0 online tool (http://gcua.schoe-dl.de/sequential_v2.html) to display the codon usage frequency and relative adaptiveness values for *Bartonella henselae* 15-kDa protein expressed in *E. coli*. The data suggest that the codon CTA (leucine) in position 84 of 15-kDa is used <20% of the time in *E.coli*. Therefore, a recombinant protein prematurely terminated at amino acid residue 84 would have a predicted molecular weight of 8-kDa. When the ~6-kDa 6×His-tag region at the amino terminus is taken into consideration, the predicted molecular weight of the recombinant protein is ~14-kDa. These predictions are in excellent overall agreement with our observations of the smaller molecular weight band which cross-reacted with the MAB against the 6×-His-tag (FIG. 13). These observations strongly support the notion that the lower molecular weight cross-reactive band seen on the Western blot is a truncated version of 15-kDa arising from the presence of the rarely used CTA codon in *E. coli*.

Example 15

Induction Studies Using Glucose Prior to IPTG

During the course our experimental work, we consistently observed very little expression of recombinant 15-kDa when host cells were grown in standard LB media prior to the addition of IPTG for inducing expression. The purified protein gave excellent discrimination between the Bartonella positive and negative patient sera, but called for frequent production of new batches of recombinant protein. These observations led us to hypothesize that this protein may be toxic to *E. coli*.

We began to identify methods for increasing the stability of the pET30/15-kDa plasmid expressed in BL21 (DE3). We maintained low levels of potentially toxic proteins expression in *E. coli* by growing the cells in LB supplemented with glucose. As shown in FIGS. 10 and 11, when 0.8% (w/w) glucose was added to the LB media prior to IPTG-induction of 15-kDa, we observed excellent overall induction of recombinant protein. We also observed similar results when 1% (w/w) glucose was used (data not shown). Noted that glucose alone (0.5% w/w) did not significantly increase protein expression (data not shown).

Example 16

Evaluation of the Recombinant 15-kDa (r15-kDa) in Binding Antibodies Present in Human Sera In order to evaluate the feasibility of using the recombinant 15-kDa antigen for the detection of *Bartonella henselae* antibodies, an ELISA was developed by coating 96-well plates with r15-kDa antigen followed by testing with human sera as described in the Experimental Protocol (see below). Human sera positive and negative for *Bartonella henselae* were obtained from Focus Diagnostics and Specialty Laboratories. Six of the positive and two of the negative samples were a generous gift from Dr. Burt Anderson (Department of Molecular Medicine, College of Medicine, University of South Florida). All samples were confirmed as positive or negative by IFA prior to their use for ELISA testing.

IgG ELISA Analysis

Figure 16:
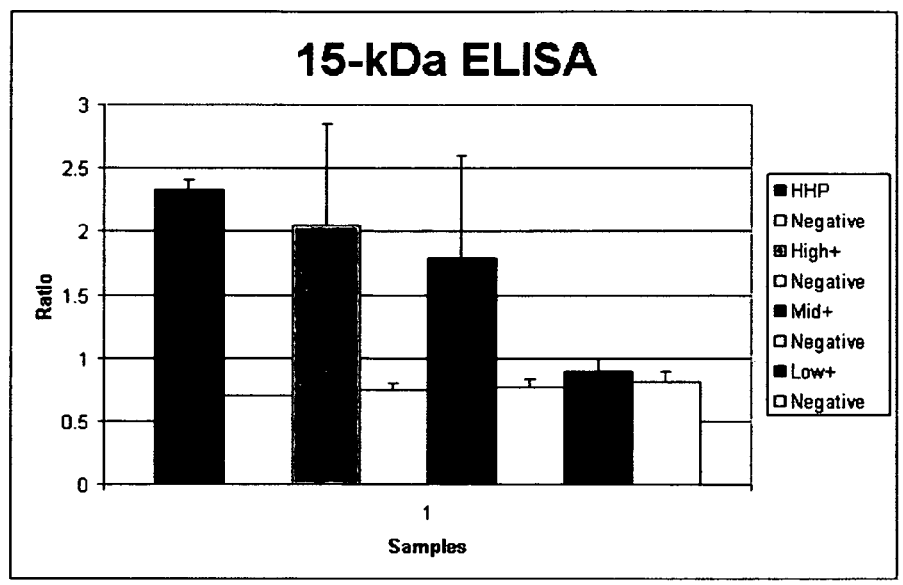
FIG. 16 illustrates ELISA data using recombinant 15-kDa protein to coat ELISA plates. Testing was carried out on four IFA positive (HHP=High high positive, High positive, Mid-positive, and Low-positive) and four (4) IFA negative patient sera samples.
Figure 17:
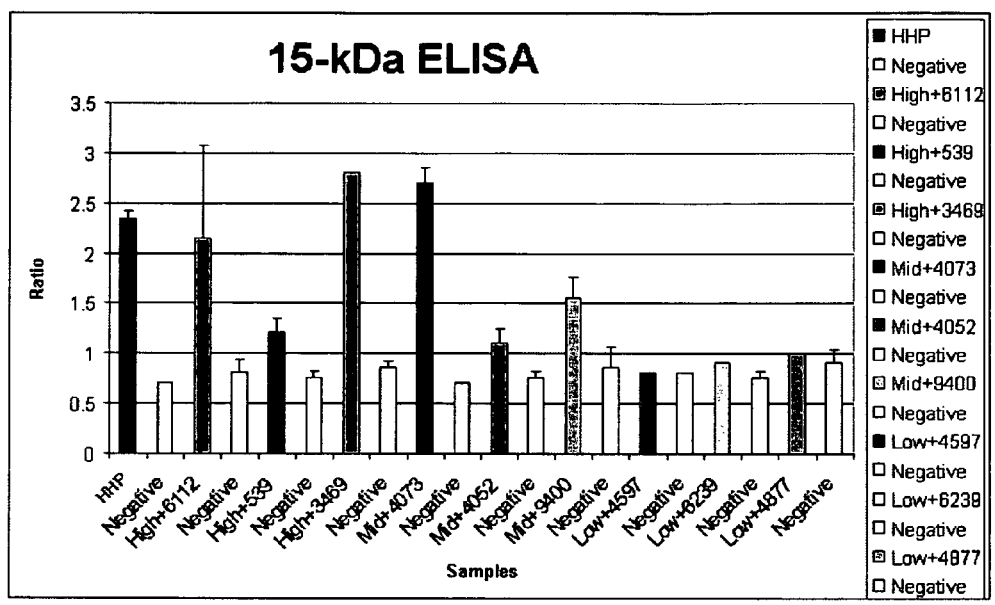
FIG. 17 illustrates IgG ELISA data using recombinant 15-kDa protein to coat ELISA plates. Testing was carried out on ten IFA positive (HHP=High high positive, High positive, Mid-positive, and Low-positive) and ten (10) IFA negative patient sera samples.

Purified recombinant 15-kDa protein was diluted in coating buffer (0.015M $Na_2CO_3$, 0.035M $NaHCO_3$, pH 9.6) and immobilized onto 96-well plates. FIGS. 16 and 17 show the IgG ELISA data using recombinant 15-kDa protein as the coating antigen on 96-well plates. FIG. 16 summarizes the data from four (4) IFA sero-positive sera and one (1) IFA sero-negative serum. 15-kDa protein binds to WA high sero-positive sera and IFA mid sero-positive sera, but fails to react to IFA low sero-positive sera and IFA sero-negative sera. FIG. 17 summarizes the data from ten (10) IFA sero-positive and one (1) IFA sero-negative patient serum. 15-kDa protein binds to IFA high sero-positive sera and IFA mid sero-positive sera, but fails to react to IFA low sero-positive sera and the IFA sero-negative serum.

IgM ELISA Analysis

Figure 18:
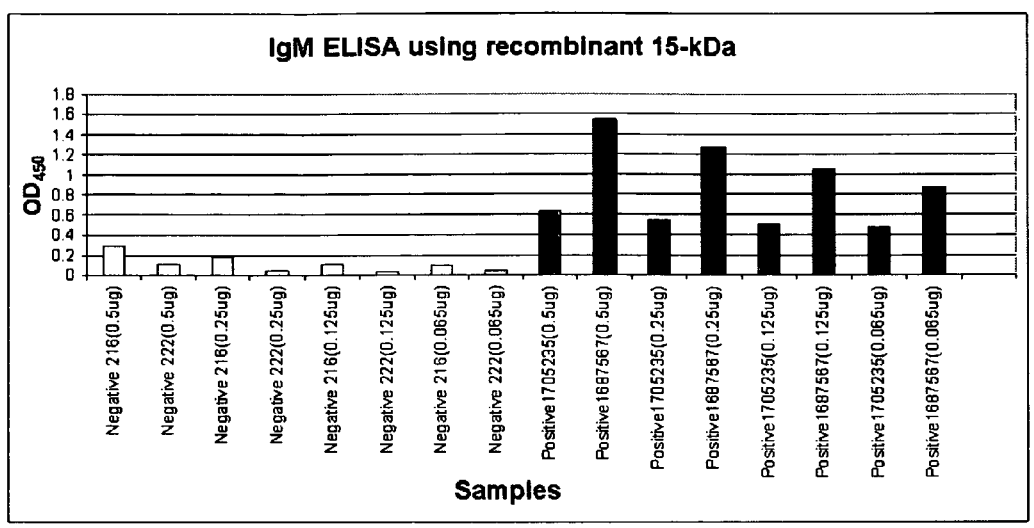
FIG. 18 illustrates IgM ELISA data using recombinant 15-kDa protein to coat ELISA plates. Testing was carried out on two (2) WA positive and two (2) IFA negative patient sera samples.

Purified recombinant 15-kDa protein was diluted in coating buffer (0,015M $Na_2CO_3$, 0.035M $NaHCO_3$, pH 9.6) and adhered to 96-well plates. FIG. 18 shows IgM ELISA data using recombinant 15-kDa purified from the insoluble fractions (i.e., inclusion bodies) as the coating antigen on 96-well plates.

FIG. 18 summarizes the data obtained from two (2) IFA sero-positive and two (2) IFA sero-negative patient samples. Four (4) varying coating concentrations of recombinant 15-kDa protein were used (see FIG. 18). Minimum levels (~5% as compared to insoluble fractions) of recombinant 15-kDa protein were present from the soluble fractions of the E. coli lysates. The purified 15-kDa recombinant protein from the soluble fractions exhibited similar IgM ELISA binding activity (data not shown).

Therefore, 15-kDa protein, when immobilized onto a surface, binds to antibodies present in IFA sero-positive sera, and has only negligible binding towards IFA-negative sera. These data suggest that 15-kDa protein is useful in detecting IgM antibody response in patients infected with Bartonella henselae.

EXPERIMENTAL PROTOCOLS (i) Amplification and Cloning of the 15-kDa Gene in Bartonella henselae Primers for the amplification of the open reading frame (ORF) (see FIG. 1) encoded within the 15-kDa gene (see FIG. 1) of Bartonella henselae Houston strain-1 from genomic DNA purchased from American Type Culture Collection (ATCC 49882) were designed according to the nucleotide sequence deposited in GenBank (GeneID: 2865504), submitted by Anderson, S. G. et al. (2004) with some modifications. The forward and reverse PCR primers included 5'LIC extensions to facilitate directional and in-frame cloning into the pET30 Ek/LIC vector (Novagen, Madison Wis.). The sequences of the forward and reverse primers were 5'-GACGACGACAAGATGTGCATTTTGTAAG-3' (SEQ ID NO: 3) and 5'-GAGGAGAAGCCCGGTTTAATTTTCACG-3' (SEQ ID NO: 4), respectively. Using these primers, the *Bartonella henselae* 15-kDa gene was amplified by gradient PCR using the following conditions: 94° C. for 2 minutes followed by 30 cycles of 94° C. for 30 seconds, a range of annealing temperatures from 48° C. to 58° C., and an extension time of 68° C. The reaction included a final annealing time of 10 min. following completion of the run. Following completion of PCR, an aliquot of the reaction was analyzed by agarose gel electrophoresis. A band of expected size (411 bp) was observed for each of the six different annealing temperatures used for the PCR reaction (FIG. 5). The remainder of each PCR reaction was treated to remove excess primers and DNA polymerase using the Wizard PCR Clean-up kit (Promega) according to the manufacture's recommended protocol.

(ii) T4 DNA Polymerase Treatment of 15-kDa Amplicon

Overhangs compatible with the pET-30 Ek/LIC cloning vector were generated on the insert DNA by T4 DNA polymerase treatment of the PCR amplicon. In brief, a reaction was set up which consisted of purified PCR product, T4 DNA polymerase buffer, dATP, DTT, and T4 DNA polymerase (LIC-qualified) in a final reaction volume of 20 μl. The reaction was started by adding enzyme, followed by incubation at room temperature for 30 minutes. The enzyme was inactivated by incubating at 75° C. for 20 minutes.

(iii) Ligation to pET30 Vector

For expression of the recombinant protein as a His-tagged fusion protein, the pET30 vector was chosen because of the presence of both a His-tag coding sequence located in-frame of the insertion site of the target protein, and the T7 promoter (FIG. 6). For annealing the vector and Ek/LIC insert, a reaction was set up consisting of pET-30 Ek/LIC vector (FIG. 6), T4 DNA polymerase treated Ek/LIC insert DNA (0.02 pmol). The reaction was incubated at room temperature for 5 minutes, followed by the addition of 25 mM EDTA. The reaction was continued for an additional 5 minutes at room temperature.

(iv) Transformation of NovaBlue *E. coli*

Transformation into NovaBlue Competent *E. coli* (Novagen) was carried out by removing the appropriate number of 20 μl aliquots of competent cells from −80° C., allowing the tubes to thaw on ice for several minutes, followed by the addition of 1 μl of the annealing reaction to the cells with gently stirring. The mixture was incubated on ice for 5 min., followed by heating of the tubes for exactly 30 seconds in a 42° C. water bath. The tikes were immediately placed on ice for 2 minutes. Following the 2 minute incubation, room temperature SOC was added, and the reactions incubated at 37° C. with shaking at 250 rpm. Cells were plated onto LB agar plates (with Kanamycin), inverted, and incubated at 37° C. overnight.

(v) Transformation of BL21 (DE3) and pLysS (DE3) *E. coli*

Transformation into BL21 (DE3) and pLysS (DE3) Competent *E. coli* (Novagen) was carried out by removing the appropriate number of 20 μl aliquots of competent cells from −80° C., allowing the tubes to thaw on ice for several minutes, followed by the addition of 1 μl of the annealing reaction to the cells with gently stirring. The mixture was incubated on ice for 5 minutes, followed by heating of the tubes for exactly 30 seconds in a 42° C. water bath. The tubes were immediately placed on ice for 2 min. Following the 2 min. incubation, room temperature SOC was added, and the reactions incubated at 37° C. with shaking at 250 rpm. Cells were plated onto LB agar plates (with Kanamycin), inverted, and incubated at 37° C. overnight.

(vi) Plasmid Mini-Preps

Plasmid DNA was isolated from transformed *E. coli* using the Wizard Plus SV Minipreps DNA Purification system (Promega) according to the manufacturer's recommended protocol.

(vii) Sequencing of Inserts

Sequence analysis was carried out on plasmid miniprep DNA using the Applied BioSystems 3130 Genetic Analyzer DNA Sequencing instrument.

(viii) Expression of 15-kDa in *E. coli*

For expression of the recombinant protein, BL21 (DE3) *E. coli* transformed with the pET30-15-kDa plasmid DNA was induced with IPTG as follows: 3 ml of LB broth cultures (with 30 μg/ml final concentration of kanamycin), supplemented with glucose (0.5%, 0.8%, 1%) were inoculated with a colony of BL21 transformed with pET30-15-kDa plasmid. Cultures were grown to mid-log phase ($OD_{600}$=0.5) at 37° C. with shaking at 250 rpm. When the cultures reached mid-log, the entire 3 ml was added to 100 ml LB (with kanamycin and glucose) and allowed to grow to mid-late log phase ($OD_{600}$=0.5-1.0). When the cultures reached mid-late log stage, they were split into two separate 50 ml batches. To one flask, 500 μl of IPTG was added (final concentration of 1 mM). No IPTG was added to the other flask which served as a control. Growth of the IPTG induced and un induced cultures were allowed to proceed for 2-3.5 hours at 37° C. with shaking at 250 rpm. Cell pellets were harvested by centrifugation at 3,000 rpm for 15 minutes at 4° C., and then processed with BugBuster Master Mix (Novagen) as described below.

(ix) Purification of Soluble Cytoplasmic and Insoluble Protein Fractions BugBuster Master Mix (Novagen) was used according to the manufacturer's protocol for isolating the recombinant antigen. Cells were harvested from liquid cultures by centrifugation at 3,000 rpm for 15 min. The cell pellets were re-suspended in 5 ml of BugBuster Master Mix (Novagen) by gentle vortexing. The resulting cell suspensions were incubated on a rotating mixer for 20 minutes at room temperature. The mixtures were centrifuged at 4° C. for 20 min. at 16,000×g to remove the insoluble cell debris. The supernatant was transferred to a fresh tube for SDS PAGE analysis. The pellet was then processed to isolate the insoluble cytoplasmic fraction, which consists of cell debris and aggregated protein (inclusion bodies). Inclusion body purification was carried out by re-suspending the pellet in the same volume (5 ml) of 1× BugBuster Master Mix used to re-suspend the original cell pellet. The mixtures were vortexed to obtain an even suspension, followed by the addition of 20 ml of 1:10 diluted BugBuster Master Mix. The suspensions were vortexed, and then centrifuged at 5,000×g for 15 min. at 4° C. to collect the inclusion bodies. The pellets were re-suspended in 15 ml of 1:10 diluted BugBuster Master Mix, vortexed, and centrifuged at 5,000×g for 15 min. This step was repeated, with the centrifugation carried out for 15 min. at 16,000×g. The supernatant was discarded, and the pellets re-suspended in 500 µl of 1×PBS. An aliquot of the purified inclusion body fraction was analyzed on an SDS PAGE gel.

(x) Purification of 15-kDa Protein

SDS PAGE analysis confirmed the presence of the expected protein band (~21-kDa) within the inclusion body fraction (FIGS. 10 and 11). Therefore, the purification of this protein was carried out from this fraction under denaturing conditions. The inclusion body pellet was re-suspended in 4 ml of denaturing lysis/binding buffer. To this mixture was added 1 ml of Ni-NTA His•Bind slurry (Novagen). The suspension was mixed gently on a rotating shaker for 1 hr. The lysate-resin mixture was carefully loaded onto a column placed over a 15 ml conical tube, and the flow-through collected and saved for later analysis (labeled as FT in FIG. 14). The column was washed with 4 ml of wash buffer collected in another 15 ml conical tube, and the fraction saved for later analysis (labeled as W1 in FIG. 14). The column was washed again with 4 ml of wash buffer, and the fraction saved for later analysis (labeled as W2 in FIG. 14). The recombinant protein was eluted with 5×0.5 ml of elution buffer (pH 5.9), and each fraction set aside for later analysis (labeled as E1-E5 in FIG. 14). Additional elutions were carried out with 5×0.5 ml of elution buffer (pH 4.5), and each fraction set aside for later analysis (labeled as E6-E10 in FIG. 14).

(xi) Buffer Compositions (All buffers were prepared fresh immediately prior to being used):

Lysis Buffer with Urea
100 mM Phosphate buffer
10 mM Tris-Cl
8 M urea;
Buffer pH adjusted to 8.0
Wash Buffer with Urea
100 mM Phosphate buffer
10 mM Tris-Cl
8 M urea;
Buffer pH adjusted to 6.3
Elution Buffer with Urea (pH 5.9)
100 mM Phosphate buffer
10 mM Tris-Cl
8 M urea;
Buffer pH adjusted to 5.9
Elution Buffer with Urea (pH 4.5)
100 mM Phosphate buffer
10 mM Tris-Cl
8 M urea;
Buffer pH adjusted to 4.5

(xii) IgG ELISA Analysis

Purified polypeptide was diluted in coating buffer (0.015M $Na_2CO_3$, 0.035M $NaHCO_3$, pH 9.6) and adhered to 96-well plates.

(xiii) IgM ELISA Analysis

Purified polypeptide was diluted in coating buffer (0.015M $Na_2CO_3$, 0.035M $NaHCO_3$, pH 9.6) and adhered to 96-well plates As will also be apparent to those skilled in the art, various combinations of the embodiments and features taught in the foregoing description are possible and can result in preferred executions of the present invention. Accordingly, it is intended that such changes and modifications fall within the scope of the present invention as defined by the claims appended hereto.

What is claimed is:

1. A method of using a recombinant 15-kDa polypeptide in an immunoassay to detect an infection of *Bartonella henselae* in a mammal, comprising the steps of:
   (a) expressing a recombinant 15-kDa polypeptide having an amino acid sequence of SEQ ID NO. 2 in an *E. coli* cell, said expressing step comprises:
      (i) introducing a 15-kDa insert DNA having a nucleotide sequence of SEQ ID NO. 1 in said *E. coli* cell;
      (ii) growing said *E. coli* cell that has said 15-kDa insert DNA;
      (iii) adding 5-10 mg/mL glucose followed by IPTG; and
      (iv) isolating said recombinant 15-kDa polypeptide,
   (b) immobilizing said recombinant 15-kDa polypeptide onto a surface;
   (c) contacting said immobilized recombinant 15-kDa polypeptide with a biological sample obtained from a mammal, said mammal is suspected of an infection of *Bartonella henselae*, under conditions that allow formation of an antibody-antigen complex; and
   (d) detecting the formation of said antibody-antigen complex,
   wherein said detected antibody-antigen complex is indicative of the presence of said antibody against *Bartonella henselae* in said biological sample, and is indicative of an infection of *Bartonella henselae* in said mammal.

2. The method according to claim 1, wherein the mammal is a human.

3. The method according to claim 1, wherein said antibody is an IgG or IgM.

4. The method according to claim 1, wherein said detecting step further comprising adding an indicator reagent comprising a signal generating compound after step (c).

5. The method according to claim 4, wherein said indicator reagent is horse-radish peroxidase.

6. A method of diagnosing an infection of *Bartonella henselae* in a mammal, comprising the steps of:
   (a) expressing a recombinant 15-kDa polypeptide having an amino acid sequence of SEQ ID NO. 2 in an *E. coli* cell, said expressing step comprises:
      (i) introducing a 15-kDa insert DNA having a nucleotide sequence of SEQ ID NO. 1 in said *E. coli* cell;
      (ii) growing said *E. coli* cell that has said 15-kDa insert DNA;
      (iii) adding 5-10 mg/mL glucose followed by IPTG; and
      (iv) isolating said recombinant 15-kDa polypeptide,
   (b) obtaining a biological sample from a mammal suspected of having a *Bartonella henselae* infection;
   (c) immobilizing said recombinant 15-kDa polypeptide onto a surface;
   (d) contacting said immobilized recombinant 15-kDa polypeptide with said biological sample, under conditions that allow formation of antibody-antigen complex;
   (e) detecting said antibody-antigen complex,
   wherein said detected antibody-antigen complex is indicative of the presence of said antibody against *Bartonella henselae* in said biological sample, and is indicative of a diagnosis of infection of *Bartonella henselae* in said mammal.

7. The method according to claim 6, wherein said mammal is either a cat or a human.

8. The method according to claim 6, wherein said antibody is an IgG or IgM.

9. The method according to claim 6, wherein the contacting step is performed at room temperature for about 1 hour.

10. The method according to claim 6, wherein said detecting step further comprising adding an indicator reagent comprising a signal generating compound after step (d).

11. The method according to claim 10, wherein said indicator reagent is horse-radish peroxidase.

* * * * *

SEQUENCE LISTING

```
<160> NUMBER OF SEQ ID NOS: 6

<210> SEQ ID NO 1
<211> LENGTH: 411
<212> TYPE: DNA
<213> ORGANISM: Bartonella henselae

<400> SEQUENCE: 1
atggtgcatt ttgtaagatg tattcagaac aagatccccc atgcactccc tatgagttca      60
tgcgttgtat ttaaaagtat ctatgagttt aaaaaaatga aacaaaaaat aacttttgtt     120
atgatcctga taattgccct tacaggctgc gcctctctta ctggccccaa aaaaccacca     180
agatgtaatg gcaaagttac ccgcgcttta aatagagata aatgggattg ggacaataaa     240
aacctcatcc tacaagaaaa aaatgtaaag cctgtcagga ctcctatcat cctcaacacg     300
ctggaaaacg aaaaagcaac agcgaccgtg acgttgaagg aaaattcatt gaattccata     360
```

```
actcgtgaaa cactccctga gaacactatg gagattgcgc gtgaaaatta a           411
```

<210> SEQ ID NO 2
<211> LENGTH: 136
<212> TYPE: PRT
<213> ORGANISM: Bartonella henselae

<400> SEQUENCE: 2

```
Met Val His Phe Val Arg Cys Ile Gln Asn Lys Ile Pro His Ala Leu
1               5                   10                  15

Pro Met Ser Ser Cys Val Val Phe Lys Ser Ile Tyr Glu Phe Lys Lys
            20                  25                  30

Met Lys Gln Lys Ile Thr Phe Val Met Ile Leu Ile Ala Leu Thr
        35                  40                  45

Gly Cys Ala Ser Leu Thr Gly Pro Lys Lys Pro Pro Arg Cys Asn Gly
    50                  55                  60

Lys Val Thr Arg Ala Leu Asn Arg Asp Lys Trp Asp Trp Asp Asn Lys
65                  70                  75                  80

Asn Leu Ile Leu Gln Glu Lys Asn Val Lys Pro Val Arg Thr Pro Ile
                85                  90                  95

Ile Leu Asn Thr Leu Glu Asn Glu Lys Ala Thr Ala Thr Val Thr Leu
            100                 105                 110

Lys Glu Asn Ser Leu Asn Ser Ile Thr Arg Glu Thr Leu Pro Glu Asn
        115                 120                 125

Thr Met Glu Ile Ala Arg Glu Asn
    130                 135
```

<210> SEQ ID NO 3
<211> LENGTH: 28
<212> TYPE: DNA
<213> ORGANISM: Bartonella henselae

<400> SEQUENCE: 3

```
gacgacgaca agatgtgcat tttgtaag                                    28
```

<210> SEQ ID NO 4
<211> LENGTH: 27
<212> TYPE: DNA
<213> ORGANISM: Bartonella henselae

<400> SEQUENCE: 4

```
gaggagaagc ccggtttaat tttcacg                                     27
```

<210> SEQ ID NO 5
<211> LENGTH: 20
<212> TYPE: DNA
<213> ORGANISM: Enterobacteria phage T7

<400> SEQUENCE: 5

```
taatacgact cactataggg                                             20
```

<210> SEQ ID NO 6
<211> LENGTH: 19
<212> TYPE: DNA
<213> ORGANISM: Enterobacteria phage T7

<400> SEQUENCE: 6

```
gctagttatt gctcagcgg                                              19
```